United States Patent
Daynes et al.

(10) Patent No.: US 6,714,817 B2
(45) Date of Patent: Mar. 30, 2004

(54) HARD PADDLE FOR AN EXTERNAL DEFIBRILLATOR

(75) Inventors: John C. Daynes, Redmond, WA (US); Judith F. Marquardt, Arlington, WA (US); Dennis R. Sequine, Monroe, WA (US)

(73) Assignee: Medtronic Physio-Control Manufacturing Corp., Redmond, WA (US)

( * ) Notice: Subject to any disclaimer, the term of this patent is extended or adjusted under 35 U.S.C. 154(b) by 121 days.

(21) Appl. No.: 09/945,229

(22) Filed: Aug. 31, 2001

(65) Prior Publication Data

US 2003/0045905 A1 Mar. 6, 2003

(51) Int. Cl.[7] .................................................. A61N 1/39
(52) U.S. Cl. ........................................... 607/5; 607/142
(58) Field of Search ................................. 607/5–8, 142, 607/145, 151, 152, 2, 119; D24/167, 168; 15/145, 22.1, 28; 451/160, 164, 174; 16/406, 422; 38/90–98

(56) References Cited

U.S. PATENT DOCUMENTS

| | | | |
|---|---|---|---|
| 1,052,077 A | * | 2/1913 | Mcmillan ..................... 279/79 |
| 3,338,587 A | * | 8/1967 | Wiley ......................... 280/623 |
| D244,153 S | | 4/1977 | Jones |
| 4,088,993 A | * | 5/1978 | LeCardonnel et al. ....... 341/133 |
| 4,097,113 A | * | 6/1978 | McKelvy .................... 439/377 |
| D252,821 S | | 9/1979 | Moore et al. |
| 4,628,935 A | | 12/1986 | Jones et al. |
| D290,396 S | | 6/1987 | Jones et al. |
| 4,705,044 A | * | 11/1987 | Deluhery et al. ............ 607/142 |
| 4,719,922 A | * | 1/1988 | Padjen et al. ................ 607/62 |
| 4,779,630 A | * | 10/1988 | Scharnberg et al. ........ 607/142 |
| 4,823,796 A | * | 4/1989 | Benson ......................... 607/7 |
| 4,915,109 A | | 4/1990 | Daynes et al. |
| D320,653 S | | 10/1991 | Jones et al. |
| D322,853 S | | 12/1991 | Benson et al. |
| 5,076,286 A | * | 12/1991 | Scharnberg ................. 607/150 |
| 5,292,338 A | * | 3/1994 | Bardy ............................ 607/5 |
| 5,321,404 A | * | 6/1994 | Mallinson et al. .......... 341/169 |
| 5,935,152 A | | 8/1999 | Merry et al. |
| 6,370,428 B1 | * | 4/2002 | Snyder et al. ................. 607/5 |
| 6,438,419 B1 | * | 8/2002 | Callaway et al. .............. 607/5 |

OTHER PUBLICATIONS

Artema Defibrillator Paddle, as early as Mar. 22, 2001.
Burdick Defibrillator Paddle, as early as Mar. 22, 2001.
Hellige Defibrillator Paddle, as early as Mar. 22, 2001.
Hewlett–Packard Codemaster 100 Defibrillator Paddle, as early as 1995.
Hewlett–Packard Sterilizable Defibrillator Paddle, as early as Mar. 22, 2001.
Nihon–Kohden TEC 7100/7200 Defibrillator Paddle, as early as 1990–1992.
PPG Defibrillator Paddle, as early as Mar. 22, 2001.
Zoll Defibrillator Paddle, as early as 1992.

\* cited by examiner

*Primary Examiner*—Angela D. Sykes
*Assistant Examiner*—Joseph S. Machuga
(74) *Attorney, Agent, or Firm*—Ingrassia Fisher & Lorenz, P.C.

(57) ABSTRACT

An electrotherapy delivery device includes an upper member having a handle portion and a pediatric electrode mounted to the bottom surface of the upper member. A base member having an adult electrode is selectively attached to the upper member with a coupling mechanism to conceal the pediatric electrode. The upper member attaches to the base member across diametrically opposed corners of the base member to provide the user with a more ergonomic hand position when accessing the paddles from the defibrillator. The device further include a plurality of switches operable to deliver a charge and to select the level of charge to be delivered to the patient. The paddle is provided with a processing circuit that receives an output from separate energy level increase and decrease switches, processes the output from the switches, and outputs a signal to the defibrillator corresponding to the level of energy selected by the switches.

38 Claims, 15 Drawing Sheets

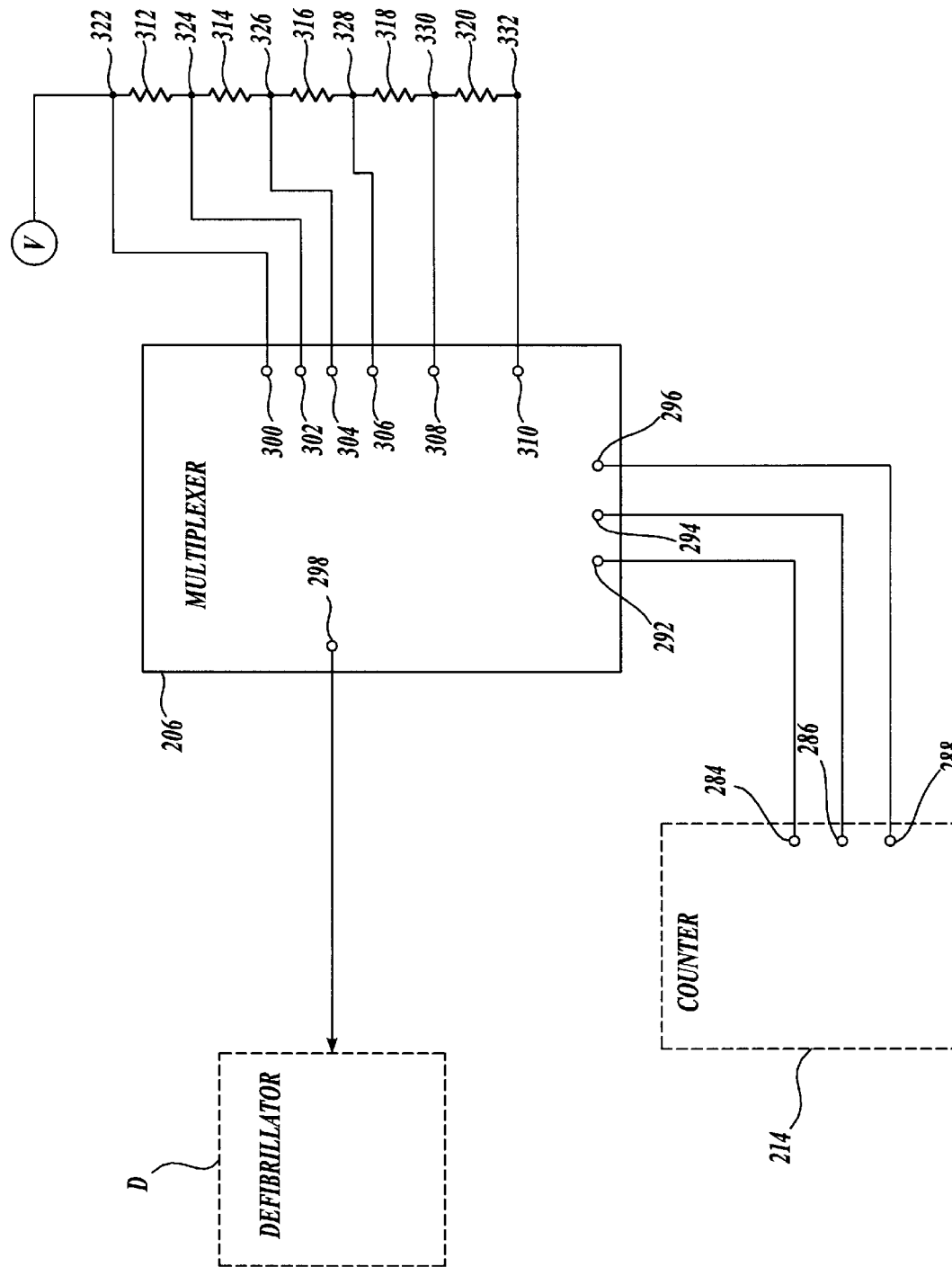

HARD PADDLE FOR AN EXTERNAL DEFIBRILLATOR

FIELD OF THE INVENTION

The present invention relates generally to medical devices, and more particularly to an electrotherapy delivery device, such as a defibrillator paddle, for use with an external defibrillator.

BACKGROUND OF THE INVENTION

One frequent consequence of heart disease is the development of cardiac arrest associated with a heart arrhythmia such as ventricular fibrillation. Ventricular fibrillation may be treated by delivering a pulse of electrical energy to the patient's heart through the use of a defibrillator. Generally described, defibrillators are devices that utilize electrical components to generate and supply electrical energy to the patient's heart in order to restore the heart to a viable rhythm.

Typically, manual external defibrillators include a pair of hand-held paddle electrodes that are used to transfer the pulse of electrical energy to the body of a patient. Present paddles known in the art, such as the paddles disclosed in U.S. Pat. No. 4,915,109 issued to Daynes et al., are usually mountable on the defibrillator, side by side, and comprise a rectangular base with a handle centrally aligned and parallel with the major axis of the base. By aligning the handle in this manner, smaller dimensioned defibrillator paddles may be fabricated, which can be mounted to the defibrillator. Accordingly, defibrillators may be designed and fabricated in smaller sizes while still being capable of stowing both paddles thereon. Other paddle electrode designs have been proposed for providing smaller paddle electrodes such as paddles having one end of the handle not connected to the base to form a cantilevered handle.

However, configuring the handles on the defibrillator paddles in these manners has created several deficiencies in the paddles. The cantilevered handle is not as mechanically robust as a handle that is connected at both ends. This can decrease the useful life of the paddle. With respect to the longitudinal aligned handle, since the base of the paddles are rectangular in shape, the handles of the paddles are aligned parallel to each other when the paddles are stowed either side by side or in-line with one another on the defibrillator. Hence, the defibrillator operator must "cock" their wrists in an awkward position in order to access the handles from the defibrillator when a patient is in need of defibrillation. Continuous "cocking" of the operators wrists during operation may be detrimental to the operator, and may reduce the effectiveness of the operator to treat the patient by increasing the time it takes to access the defibrillator paddles.

Therefore, the need exists for smaller defibrillator paddles that are stowable on the defibrillator which are comfortable to grasp when the need arises to resuscitate a patient.

SUMMARY OF THE INVENTION

In accordance with the present invention, a pair of electrotherapy delivery devices such as a defibrillator paddles are presented which overcome the deficiencies in the prior art. Each electrotherapy delivery device comprises a base member of substantially rectangular shape having a bottom surface. An electrode is coupled to the bottom surface of the base member which is operable for delivering an electrical charge supplied to the electrode to a patient. The device also includes an upper member that defines a handle portion, where the upper member is selectively coupled to the base member such that the handle portion is disposed across diagonally opposed corners of the base members. The device further includes at least one switch mechanism that is disposed within the upper member.

In accordance with another aspect of the present invention, an energy selection processing circuit is provided which comprises a digital controller for receiving a selected energy level output from energy selector switches and transmitting a digital signal corresponding to the selected energy level output. The processing circuit also includes a multiplexer for receiving the digital signal corresponding to the selected energy level output. The multiplexer determines the selected energy level based on digital signal, and outputs a variable signal corresponding to the selected energy level to the defibrillator.

In accordance with yet another aspect of the present invention, an electrotherapy delivery device is provided which comprises an adult electrode assembly having a bottom surface. A first electrode is mounted to the bottom surface of the adult electrode assembly. The device also includes a pediatric electrode assembly defining a handle portion and a mounting portion. The pediatric electrode assembly is selectively coupled to the adult electrode assembly. A second electrode is mounted to the mounting portion. A switch is disposed within the device and is in electrical communication with the second electrode. The mounting portion is smaller than the bottom surface of the adult electrode assembly.

In accordance with still yet another aspect of the present invention, a defibrillator system is provided which comprises a defibrillator that generates a charge to be delivered to a patient. Charge delivery devices are also included for transmitting the charge generated by the defibrillator. The charge delivery devices are stowable on a top surface of the defibrillator and include a substantially rectangular base member. A handle is selectively coupled to the base member and an electrode is coupled to the base member. The handle is disposed from diagonally opposed corners of the base member.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 10 is a circuit diagram of a multiplexer illustrated in the energy select circuit of FIG. 5.

DETAILED DESCRIPTION OF THE PREFERRED EMBODIMENT

Figure 1A:
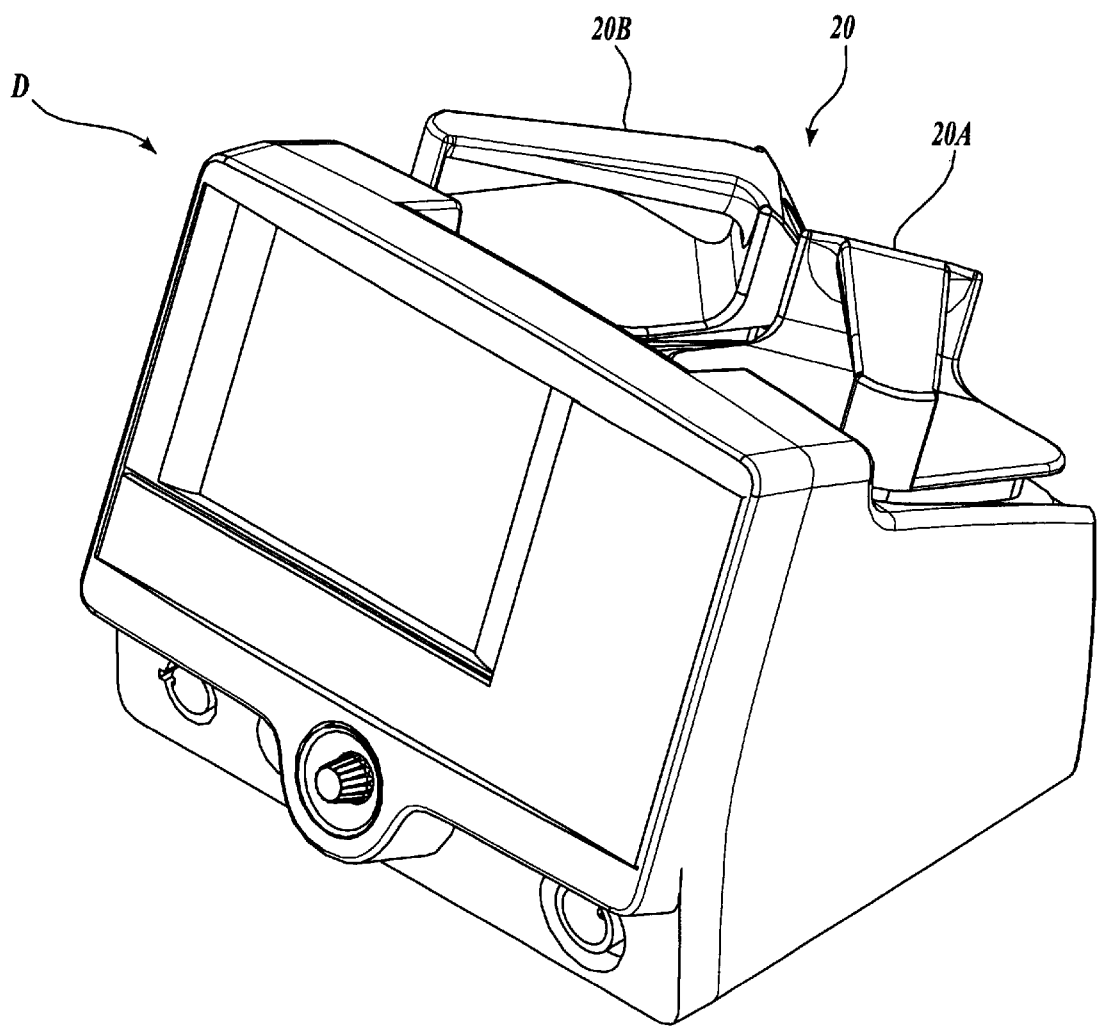
FIGS. 1A and 1B are perspective views of a defibrillator incorporating defibrillator paddles in accordance with aspects of the present invention.
Figure 1B:
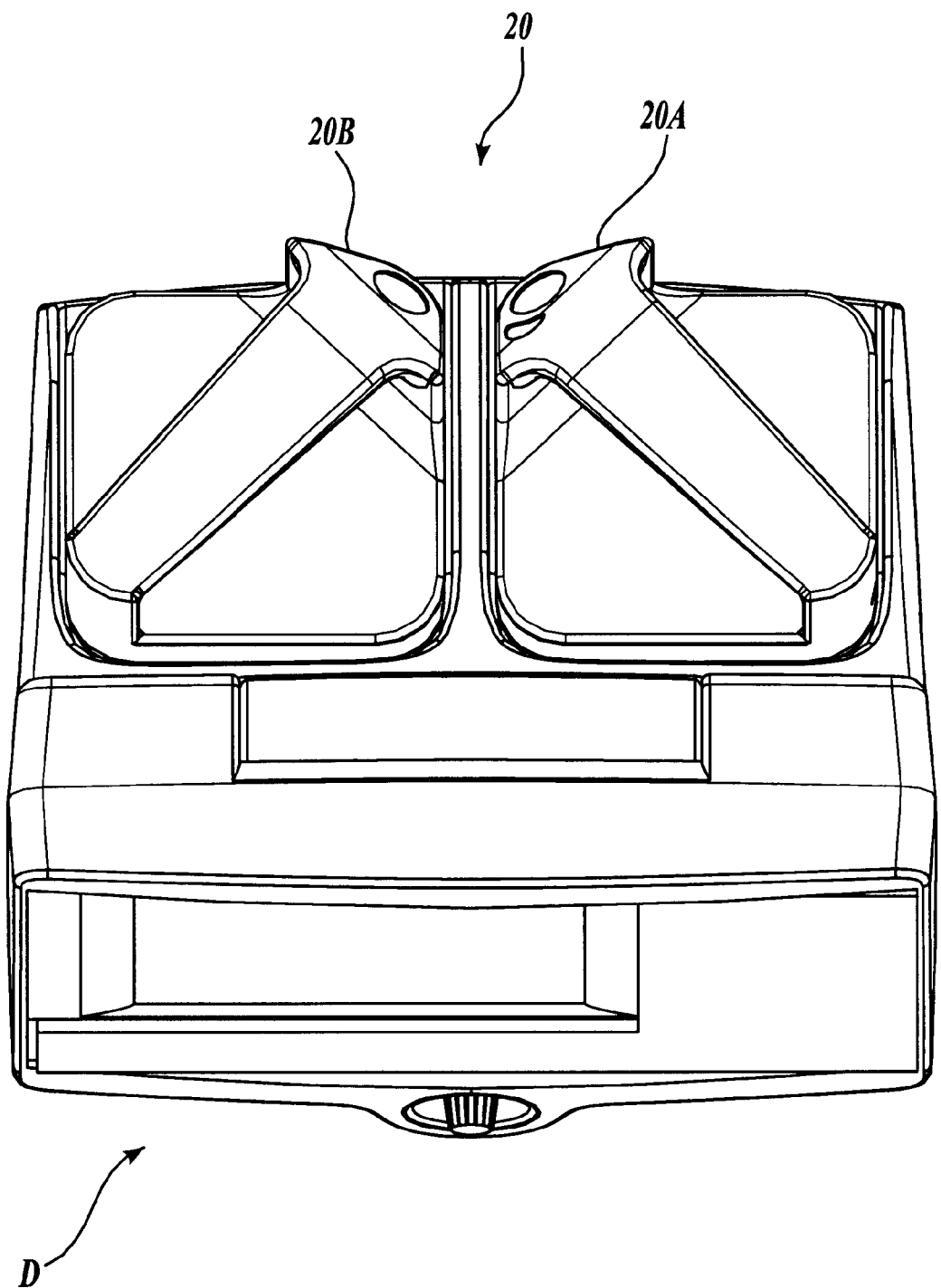

The present invention will now be described with reference to the accompanying drawings where like numerals correspond to like elements. Referring generally to FIGS. 1A and 1B, a defibrillator D is shown equipped with a pair of electrotherapy delivering devices, such as a pair of defibrillator paddles 20A and 20B, constructed in accordance with the present invention. As shown, the paddles (labeled generally as item 20) are stowed at a convenient location on a downward sloping portion of the top surface of the defibrillator D so that the paddles may be easily accessed when needed to defibrillate a patient. In operation, the paddles 20 are grasped by the defibrillator operator and placed on the body of a patient that is experiencing cardiac fibrillation. The paddles, which are connected to the defibrillator D, are held against the chest cavity of the patient and an activation switch is operated to administer an electrical shock generated by the defibrillator D so that a normal heartbeat may resume.

The pair of paddles 20 comprises an apex paddle 20A and a sternum paddle 20B. For clarity, the following description will refer to a singular paddle 20 since the paddles are substantially identical. When the need arises, distinctions will be made to differentiate the apex paddle 20A from the sternum paddle 20B and vice versa.

Figure 2A:
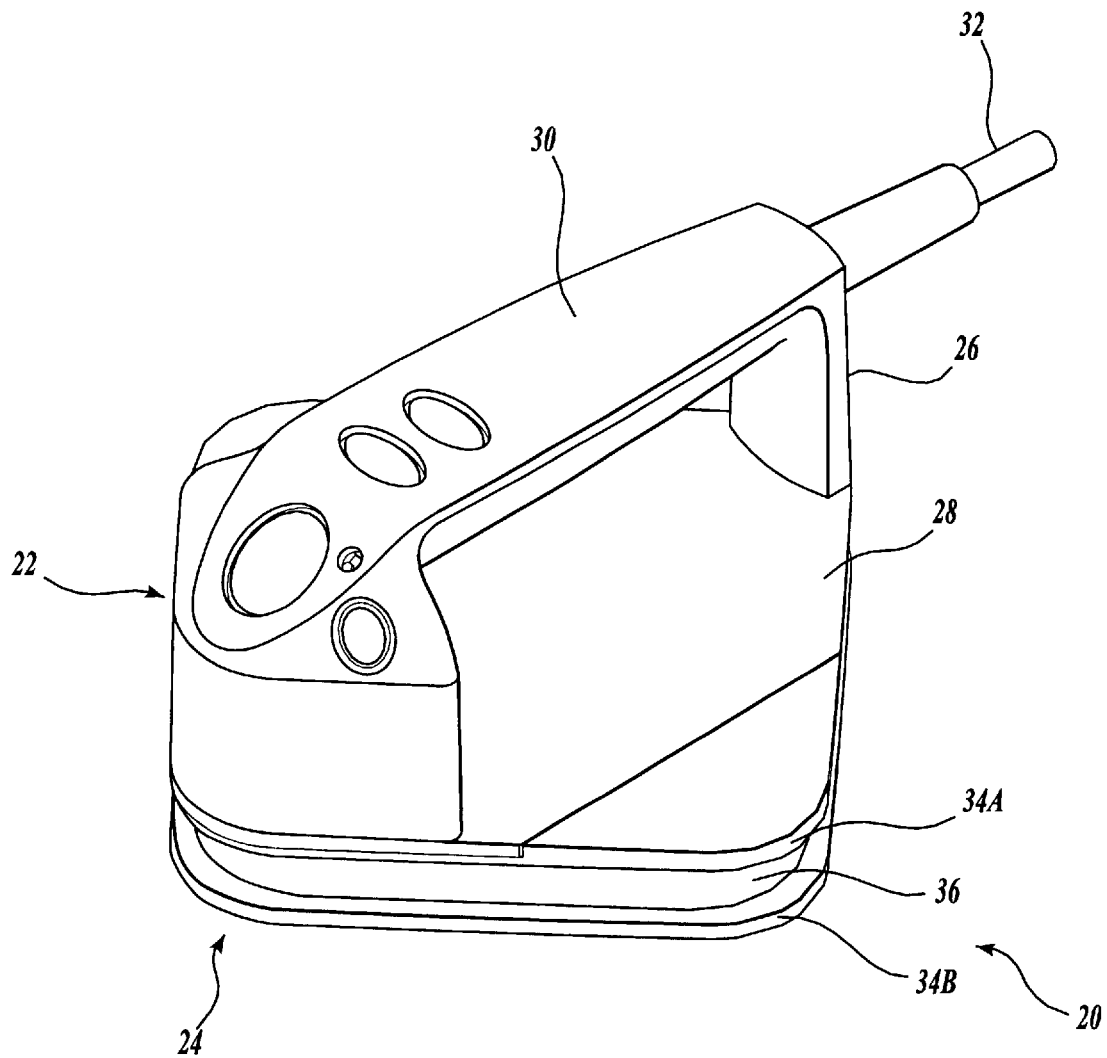
FIG. 2A is a top perspective view of a defibrillator paddle in accordance with aspects of the present invention.
Figure 2B:
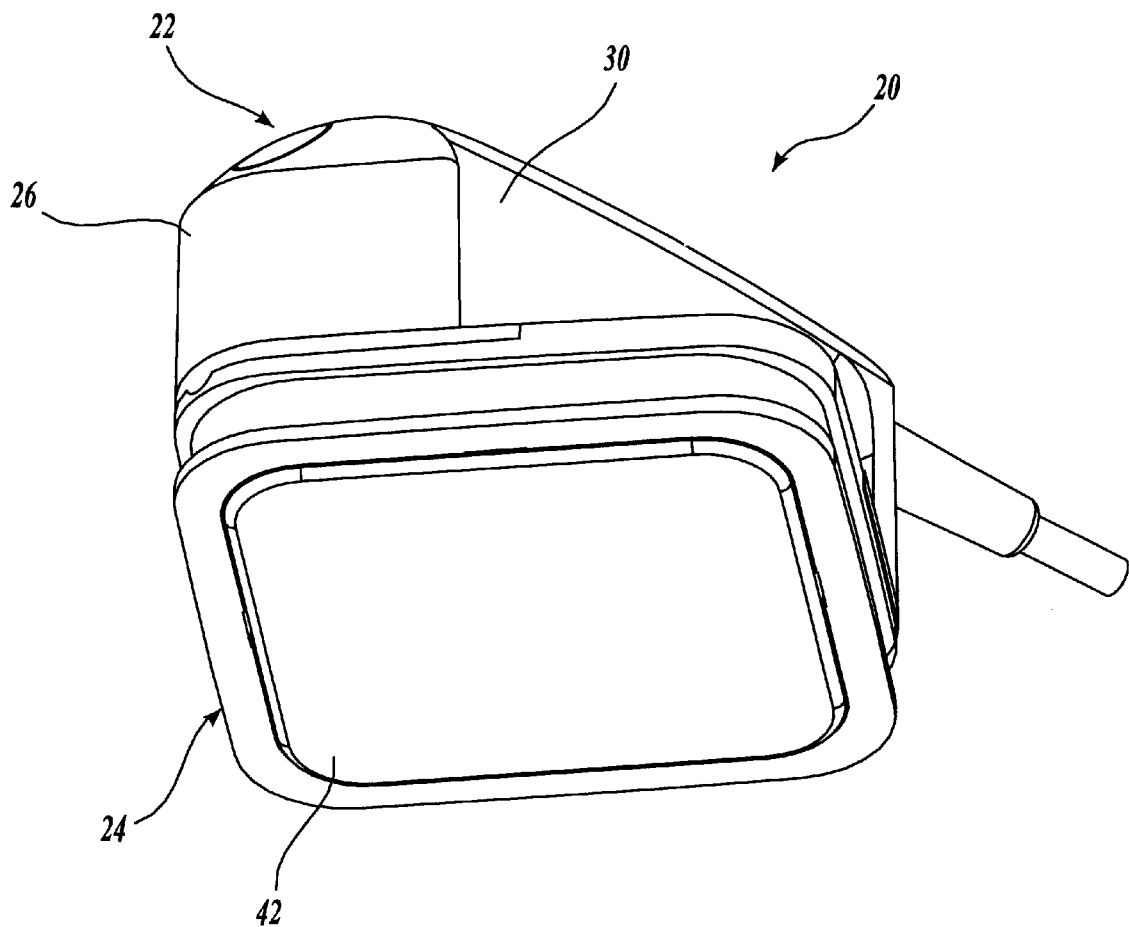
FIG. 2B is a bottom perspective view of a defibrillator paddle in accordance with aspects of the present invention.
Figure 3A:
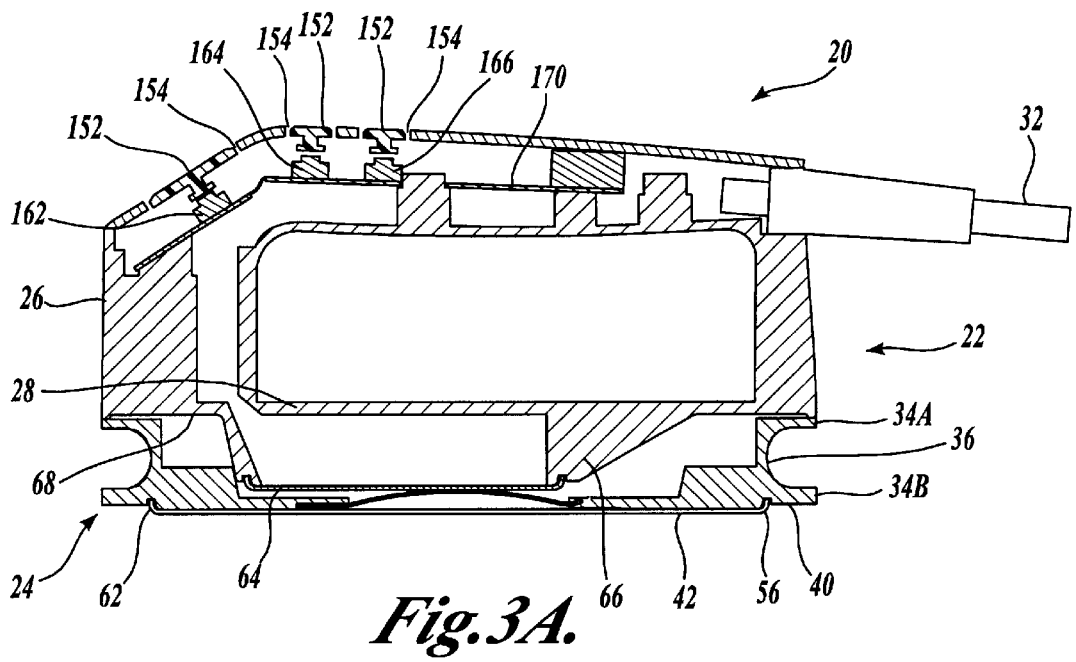
FIGS. 3A and 3B are cross-sectional views of the defibrillator paddle shown in FIG. 2A.

Referring now to FIGS. 2A and 2B, the paddle 20 includes an upper member 22 and a base member 24. The upper member 22 of the paddle 20 includes an upwardly extending, generally U-shaped handle portion 26 and a generally platelike mounting portion 28 to which the handle portion 26 is secured. The handle portion 26 defines a graspable middle portion 30 that can easily be grasped by the defibrillator operator. As best shown in FIG. 3A, the upper surface of the middle portion slopes slightly downward as it extends from the front of the paddle 20 to the rear of the paddle 20. The middle portion 30 is further made slightly thicker at its center region and may include finger slots or other moldings to aid the user in quickly and properly grasping the paddles. Attached to the rear of the handle portion 26 is an electrical cord 32, which connects the paddle 20 to the defibrillator.

Referring back to FIG. 2A, the base member 24 is located below the upper member 22 of the paddle 20 and is selectively connected to the upper member 22 through a coupling mechanism which will be described in more detail below with reference to FIGS. 2C, 2D, and 4A–4C. In one embodiment, the base member 24 has a generally rectangular shaped body and is oriented such that the handle portion 26 of the upper member 22 is aligned across diametrically opposed corners of the base member 24, the importance of which will be described below. While shown in FIG. 2A as generally rectangular in shape, the base member 24 can be of any size or polyhedral shape without departing from the scope of the present invention. The base member 24 includes an upper plate 34A of substantially rectangular geometry that extends outwardly from each side of the upper member 22. Spaced apart and substantially parallel to the upper plate is a lower plate 34B of a size and geometry similar to the upper plate 34A. The upper plate 34A and lower plate 34B are connected by a continuous upwardly extending side wall 36. As best shown in FIG. 3A, the side wall 36 has a channel-like arcuate cross-section that extends around the circumference of the base member 24, thus giving the upper and lower plates 34A, 34B the appearance of two parallel, spaced-apart flanges. Attached to the bottom surface 40 of the lower plate 34B is an electrically conductive electrode 42.

Figure 2C:
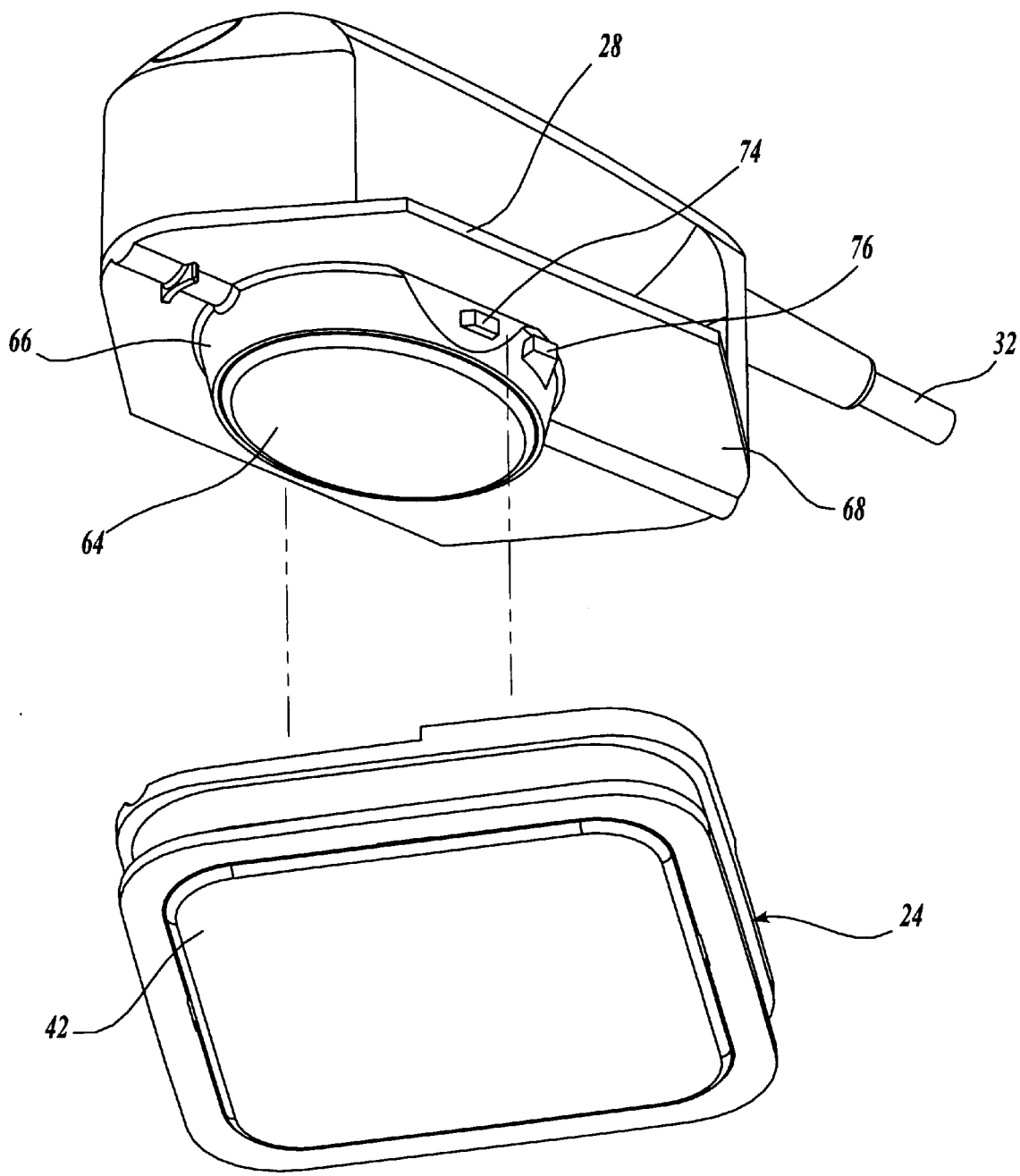
FIG. 2C is a bottom perspective view of the paddle in FIG. 2B having a base member separated therefrom.
Figure 2D:
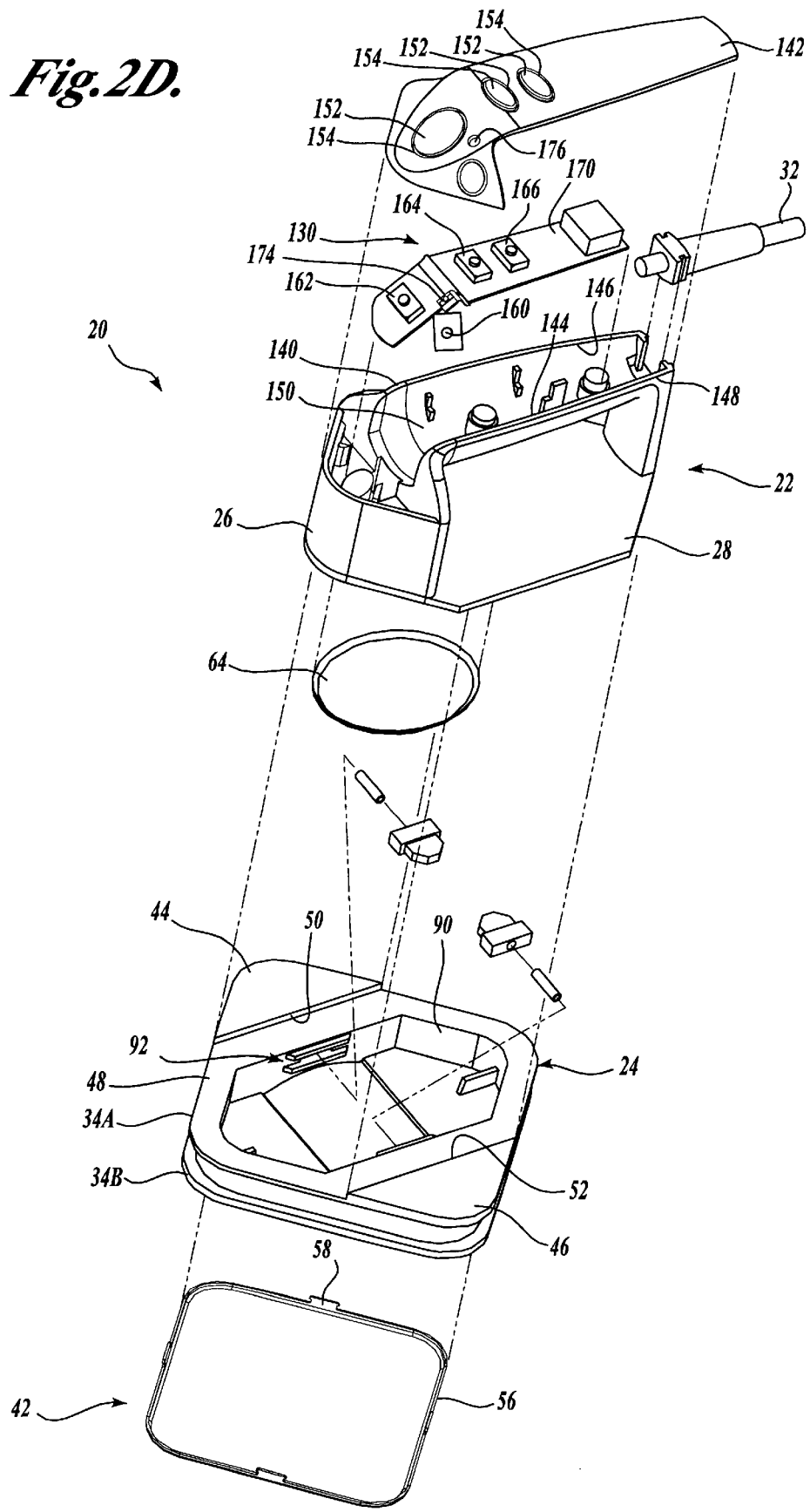
FIG. 2D is an exploded assembly view of the defibrillator paddle shown in FIG. 2A.

Referring to FIG. 2D, the upper plate 34A includes two shoulder portions 44 and 46 positioned at diametrically opposed corners of the base member 24 which define a recess 48 therebetween for receiving the mounting portion 28 of the upper member 22. In the embodiment shown, each shoulder portion 44 and 46 is generally triangular in shape and includes inward facing side walls 50 and 52, respectively, which are parallel to each other. The geometry of the circumference of the mounting portion 28 corresponds to the geometry of the recess 48 to allow for the mounting portion 28 to mate with the base member 24 when retained by a coupling mechanism. The recess 48 is positioned such that when the base member 24 and the upper member 22 are mated, the handle portion 26 is aligned with diametrically opposed corners of the base member 24. The height or thickness of the shoulder portions 44 and 46 and the mounting portion 28 are such that when the components are mated, their upper surfaces are flush and thereby resemble a unitary paddle.

Still referring to FIG. 2D, the electrode 42 is dimensioned slightly smaller than the base member 24 and is attached to the bottom surface of the base member 24 by any suitable fastening means. In one embodiment, the electrode 42 is generally rectangular in shape. However, it will be appreciated that the electrode 24 can be of any size or shape without departing from the scope of the present invention. Additionally, the electrode 24 need not be the same shape as the base member 24. The electrode 42 is made from an electrically conductive material so as to transmit the pulse of electrical energy from the defibrillator. In the embodiment shown, the electrode 42 includes a perimeter lip 56 and side tabs 58 extending upwardly therefrom. As best shown in FIG. 3A, the base member 24 includes a circumferential groove 62 positioned in the bottom surface 40 to receive the lip 56 of the electrode 42. The base member 24 further includes slots (not shown) of a slightly smaller dimension for receiving the tabs 58 of the electrode 42 to couple the electrode 42 to the bottom surface of the base member 24 via a force fitting arrangement. The electrode 42 is in electrical communication with the electrical cord 32 so as to supply the patient with an electrical charge generated by the defibrillator. Various electrical connections are possible. One embodiment is described below with reference to FIGS. 2d, 3A and 3B.

Figure 3B:
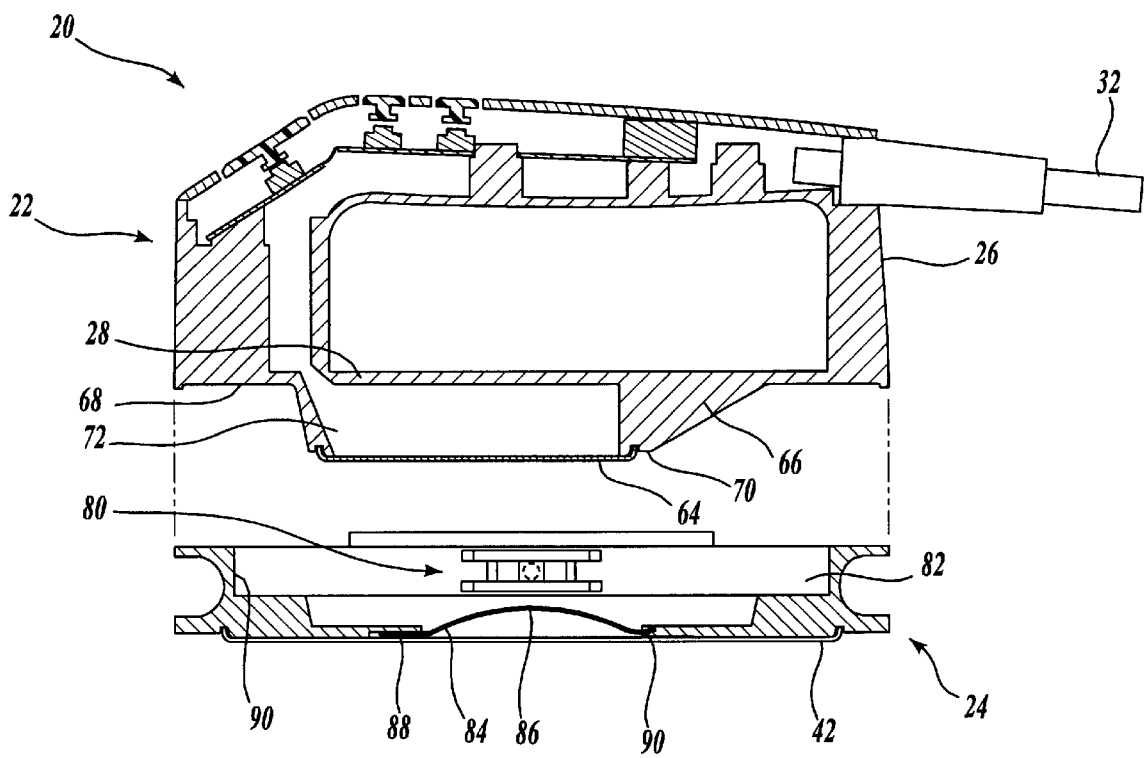

In accordance with an another aspect of the present invention, shown in FIGS. 2C, 3A, and 3B is a second electrically conductive electrode 64 of relatively small dimensions attached to the underside of the mounting portion 28 through a generally cylindrical boss 66. The boss 66 and second electrode are nestable within the removable base member 24. To reveal the second electrode 64, the base member 24 of the paddle 20 is selectively detached from the upper member 22 of the paddle 20 by operation of a coupling mechanism generally designated as item 80. Based on the physical dimensions of the patient, the base member 24 can be attached to the upper portion 22 of the paddle 20 when the patient is an adult or can be removed to reveal the smaller second electrode 64 when the patient is of a younger age. Thus, base member 24 may be referred to as an adult electrode assembly, and the second electrode 64 may be referred to as a juvenile or pediatric electrode assembly.

Still referring to FIGS. 2C, 3A, and 3B, the cylindrical boss 66 extends downwardly from the bottom surface 68 of the mounting portion 28. The boss 66 has a generally flat bottom surface 70 (see FIG. 3B) that includes an aperture 72 extending up through the boss 66 and into the handle portion 26 of the upper member 22. The boss 66 also includes two linearly space-apart rib portions 74 and 76 (see FIGS. 4A and 4B) that project outwardly from each side surface of the boss 66. In the embodiment shown, each rib portion 74 includes a tapered surface for engagement with a latch member. The rib portions 74 and 76, along with the latch member, form a portion of the coupling mechanism 80, the operation of which will be described in more detail below. Mounted to the bottom surface 70 of the boss 66 in spaced relation from the handle portion 26 is the second electrode 64, sometimes referred to as a pediatric electrode, which is smaller than electrode 42, sometimes referred to as an adult electrode. The second electrode 64 can be attached to the boss 66 by any suitable fastener, and can be attached to the boss in a similar manner as the electrode 42 is attached to the base member 24 described above. The second electrode 64 is in electrical communication with the electrical cord 32 by electrical connectors such as wires disposed within the aperture 72. In one embodiment, the second electrode is generally oval in shape. However, it will be appreciated that the second electrode may be of any size or shape suitable for a pediatric application.

Referring now to FIG. 3B, to accommodate the downwardly extending boss 66 and second electrode 64, the base member 24 includes a centrally located cavity 82 having an opening at its upper and lower ends. Mounted within the opening at the lower end of the cavity 82 is a plate spring 84 for providing an electrical connection between the second electrode 64 and the electrode 42 when the base member 24 is attached to the upper member 22. The plate spring 84 has a shape corresponding to the lower end opening and includes an upwardly extending arcuate contact portion 86 and a pair of lower contact portions 88 and 90. When the base member 24 is mounted to the upper member 22 to function as an adult paddle, the plate spring 84 is compressed firmly between the bottom surface of the second electrode 64 and the top surface of the electrode 42 to provide electrical communication therebetween. The plate spring 84 also prevents looseness and stabilizes the mounting of the base member 24 on the mounting portion 28 of the upper member 22 of the paddle 20.

As best shown in FIGS. 2D and 3B, the cavity 82 is defined by a circumferentially extending inner side wall 90 and is shaped substantially similar to, but smaller than, the perimeter of the mounting portion 28 of the upper member 22. Located on diametrically opposed inner side walls and spaced inward from and below the inner side walls 50 and 52 of shoulder portions 44 and 46 are sets of rail members 92. Each set of rail members 92 includes two spaced-apart elongate ribs, both rails being parallel to the upper and lower plates 34A and 34B. The rail members 92 form a portion of the retaining mechanism 80. Centrally located between each set of rail members 92 is a slot 100 (FIGS. 4A–4C) for receiving a biased actuating latch member 102.

Figure 4A:
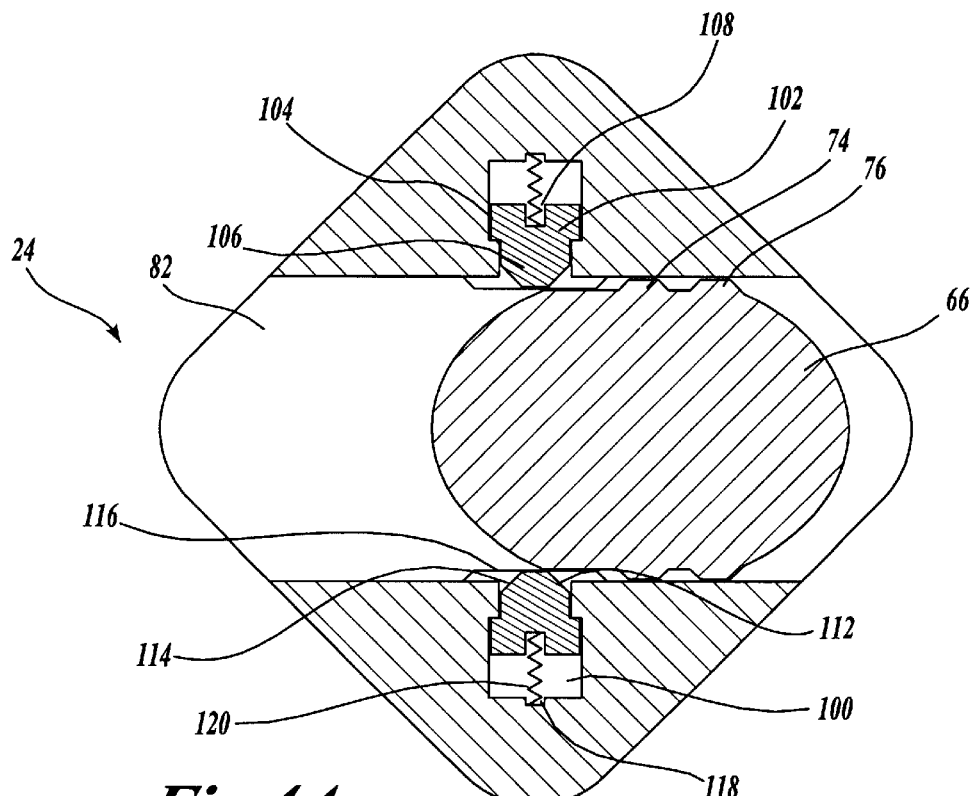
FIGS. 4A–4C are cross-sectional views of a schematic representation of a coupling mechanism formed in accordance with aspects of the present invention.
Figure 4B:
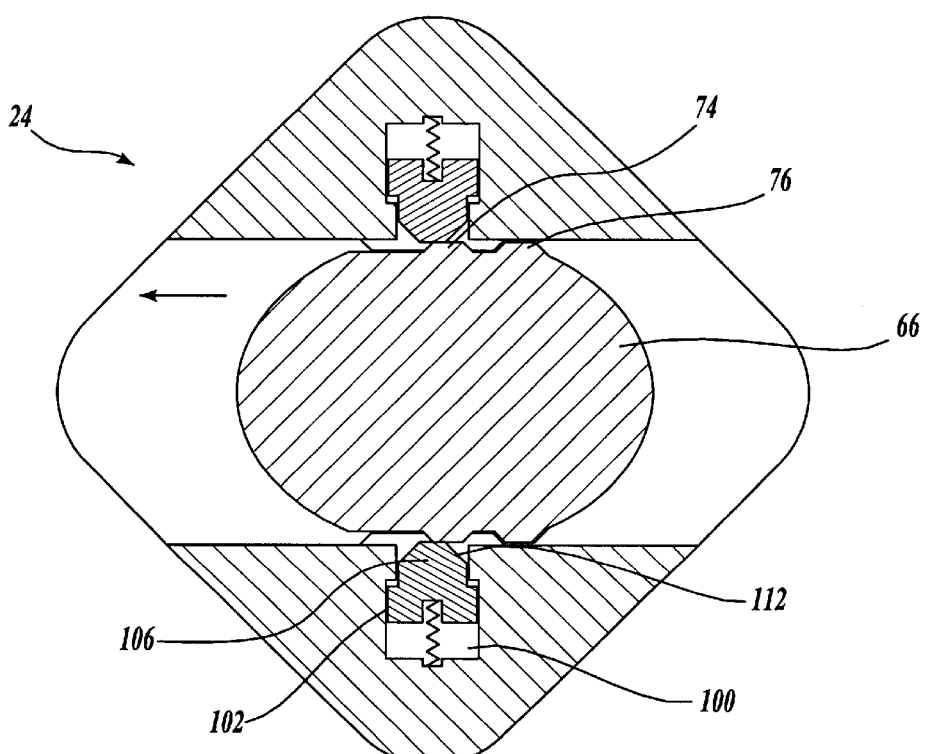
Figure 4C:
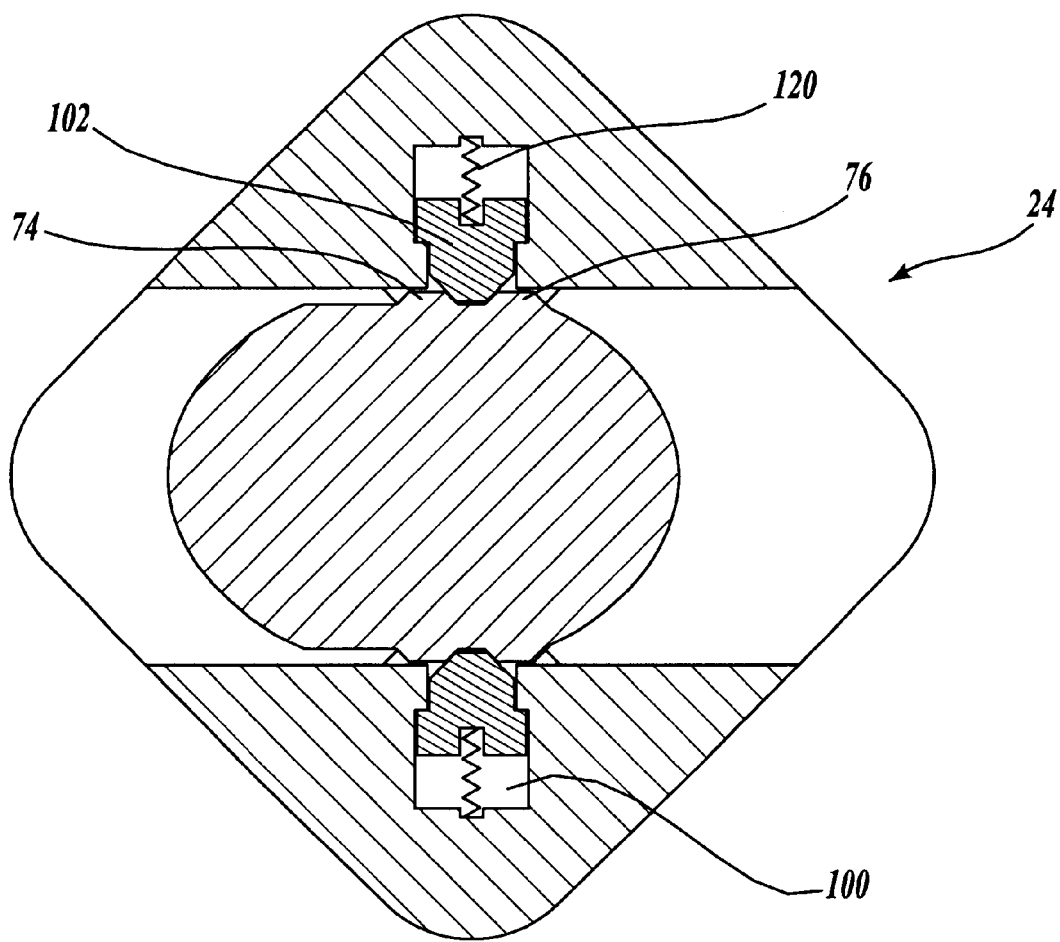

In the embodiment of FIGS. 4A–4C, the latch member 102 includes a rectangular base portion 104 and a spade-shaped protruding portion 106 connected thereto. The base portion 104 includes a bore 108 having an opening 110 at its rear surface. The protruding portion 106 defines two camming surfaces 112 and 114 and a central engagement surface 116. Connected to the slot 100 is a bore 118 for receiving a biasing member 120 such as a spring. The biasing member 120 is suitably dimensioned to engage the end of the bore 118 and to be received within the bore 108 located within the latch member 102. The biasing member 120 biases the latch members 102 radially inward into the cavity 82. The sets of rail members 92 and the latch members 102, along with the rib portions 74 and 76 of the boss 66 described above, form the coupling mechanism 80.

To couple the upper member 22 of the paddle 20 to the base member 24 of the paddle 20, the paddle operator holds the upper member 22 in one hand and the base member 24 in the other hand. See FIGS. 4A–4C. As the upper member 22 is lowered straight down into the base member 24 with the mounting portion 28 parallel with the upper plate 30 of the base member 24, the upper member 22 is aligned slightly off center in the rearward direction, parallel to the inward facing side walls 50 and 52 of the shoulder portions 44 and 46 as best shown in FIG. 4A. As the upper member 22 is lowered into engagement, the cavity 82 within the base member 24 accommodates the downwardly protruding boss 66.

Once the mounting portion 28 is flush with the shoulder portions 44 and 46, the operator slides the upper member forward in the direction illustrated by the arrow, parallel to the shoulder side walls 50 and 52, as best shown in FIG. 4B. The rib portions 74 and 76 of the boss 66 are positioned on the boss such that when the mounting portion 28 is flush with the base member 24, each rib portion 74 and 76 will be aligned in elevation between each set of rail members 92 on base member 24. When the operator slides the upper member 22 forward relative to the base member 24, the rib portions 74 and 76 slide between the rail members 92. In doing so, the tapered surface of the rib portions 74 engage the camming surface 112 of the protruding portion 106 of latch members 102, thereby displacing the latch members 102 orthogonally into the slots 100 of the base member 24 and compressing the biasing member 120.

As shown in FIG. 4C, once the first rib portions 74 pass the latch members 102, the latch members 102 translate linearly inward by the force of the biasing member 120 and rest between the rib portions 74 and 76 and the rail members 92, thereby coupling the upper member 22 of the paddle 20 onto the base member 24 of the paddle 20. It will be appreciated that to separate the base member 24 from the upper member 22, the above process is reversed. The upper member 22 is slid backwards, in a direction opposite that used during the attachment process, and then lifted out of the base member 24 to expose the second electrode 64.

While one suitable embodiment of the coupling mechanism has been described above with reference to FIGS. 4A–4C, it should be readily evident that other coupling mechanisms could be used to suitably couple the upper portion of the paddle to the base portion of the paddle.

A defibrillator paddle constructed in accordance with the present invention presents numerous advantages over the prior art. The paddle provides enhanced hand position over previous paddles by aligning the handle with the diametrically opposed corners of the base member. This configuration allows the manufacturer of paddles and defibrillators to design and fabricate smaller paddles and external defibrillators while eliminating the awkward "cocking" position of the wrists when accessing the paddles from the defibrillators. Additionally, when the paddle of the present invention is used as a pediatric paddle (i.e. the base member is separated from the upper member), the mounting plate of the upper member specifically provides a smaller "footprint" so that the paddles may be placed closer together to treat a child whose chest is of a smaller dimension than an adults. Further, the base member of the present invention is preferably symmetrical so that the base member can be positioned from either direction when attaching to the upper member. This leads to faster assembly time of paddle into an adult assembly which translates into quicker treatment of the patient.

In accordance with other aspects of the present invention, the handle portion 26 of the paddle 20 preferably includes various switches to operate functions of the defibrillator, such as discharging a pulse of electrical energy. Referring back to FIGS. 2D and 3A–3B, the handle portion 26 is broken into a base 140 and a cover 142 to accommodate switches 130. The base includes two diametrically opposed upwardly extending side walls 144 and 146 having an outer peripheral rim 148 which defines a semi-tubular cavity 150. The cavity 150 is of a suitable dimension to receive the necessary components of the switches 130. Both ends of the cavity 150 are open, with the rearward end being open for receiving the electrical cord 32 and the frontward end being open for permitting access for wiring to and from the second electrode 64. Switch actuators 152, such as push buttons or the like, are mounted within apertures 154 located in the cover 142 of the handle portion 26. The actuators 152 actuate the switches 130. The cover 142 is removably secured to the base 140 via conventional fasteners such as screws or the like. Each switch actuator 152 mounted within the handle portion may be equipped with tactile feedback means, not shown but well known in the art. Moreover, it will be appreciated that the switch mechanisms 130 can be utilized by the defibrillator operator for controlling any combination of desirable functions such as those described in more detail below.

As shown in FIG. 2D, an illustrative embodiment of the paddle 20 includes a plurality of switches 130 which can include, but is not limited to, a charge switch 160, an activation or trigger switch 162, and energy level selector switches 164 and 166. Other switches can also be utilized such as a print switch. One energy level selector switch 164 may be used to increase the amount of charge produced by the defibrillator D, while the other energy level selector switch 166 decreases the amount of charge produced by the defibrillator D. The selected charge amount is then applied to the patient through the electrodes (42 or 64) by activation of the trigger switch 162 disposed in both the apex and sternum paddle. In one embodiment of the present invention, the apex paddle 20A includes a charge switch, a trigger switch, and energy increase and energy decrease switches. The sternum paddle 20B includes a trigger switch and a print switch. However, it will be appreciated by those skilled in the art that the switch complement on the apex paddle 20A can be disposed in the sternum paddle 20B, and vice versa.

The various switches 130 are mounted to a circuit board 170 positioned within the cavity 150 of the handle portion 26 so that the switches align with the corresponding switch actuators 152. It will be appreciated by those skilled in the art that the switch actuators 152 can be attached to the cover 142 of the handle portion 26. Alternatively, the switch actuators 152 may be attached to the switch mechanisms 130 and extend through the apertures 154 in the cover 142 of the handle portion 26. The circuit board 170 is in electrical communication with the cord 32 to send signals such as energy select voltages to the defibrillator. Likewise, the circuit board 170 is in electrical communication with the electrode 64, and the electrode 42 via the plate spring 84, to delivery electrotherapy, such as a pulse of electrical energy, from the defibrillator to the fibrillating patient through cord 32. The paddle 20 can further include a charge-ready or defibrillator-ready indicator 174, such as an LED, connected to the circuit board 170 and viewable through a dedicated opening 176 in the cover 142 of the handle portion 26 of paddle 20 to indicate when the defibrillator is "ready" to deliver the specified selected charge.

The paddle 20 of the present invention may be used with preexisting defibrillators such as the LIFEPAK® 12 external defibrillator manufactured by Medtronic Physio-Control Corp, the assignee of the present invention. Preexisting defibrillators such as the LIFEPAK® 12 external defibrillator have used a rotary switch in the defibrillator paddle to set a defibrillation energy. Accordingly, software on the preexisting defibrillators is capable of interpreting the amount of energy selected by receiving a digital signal from an analog to digital ("A/D") converter that processes the variable analog output of the rotary switch. Therefore, to be compatible with the software and A/D converter of the LIFEPAK® 12 external defibrillator and other pre-existing defibrillators, the paddle needs to output a single analog voltage signal indicative of the selected level of energy to be generated by the defibrillator and delivered to the patient. As will be described in more detail below, the paddle 20 is equipped with an energy select circuit 200 and energy select switches that are capable of outputting an analog signal to the defibrillator that may be utilized by the software loaded in preexisting defibrillators, such as the LIFEPAK® 12 external defibrillator, to generate the selected level of electrical energy to be delivered to the patient via the paddle 20.

Figure 5:
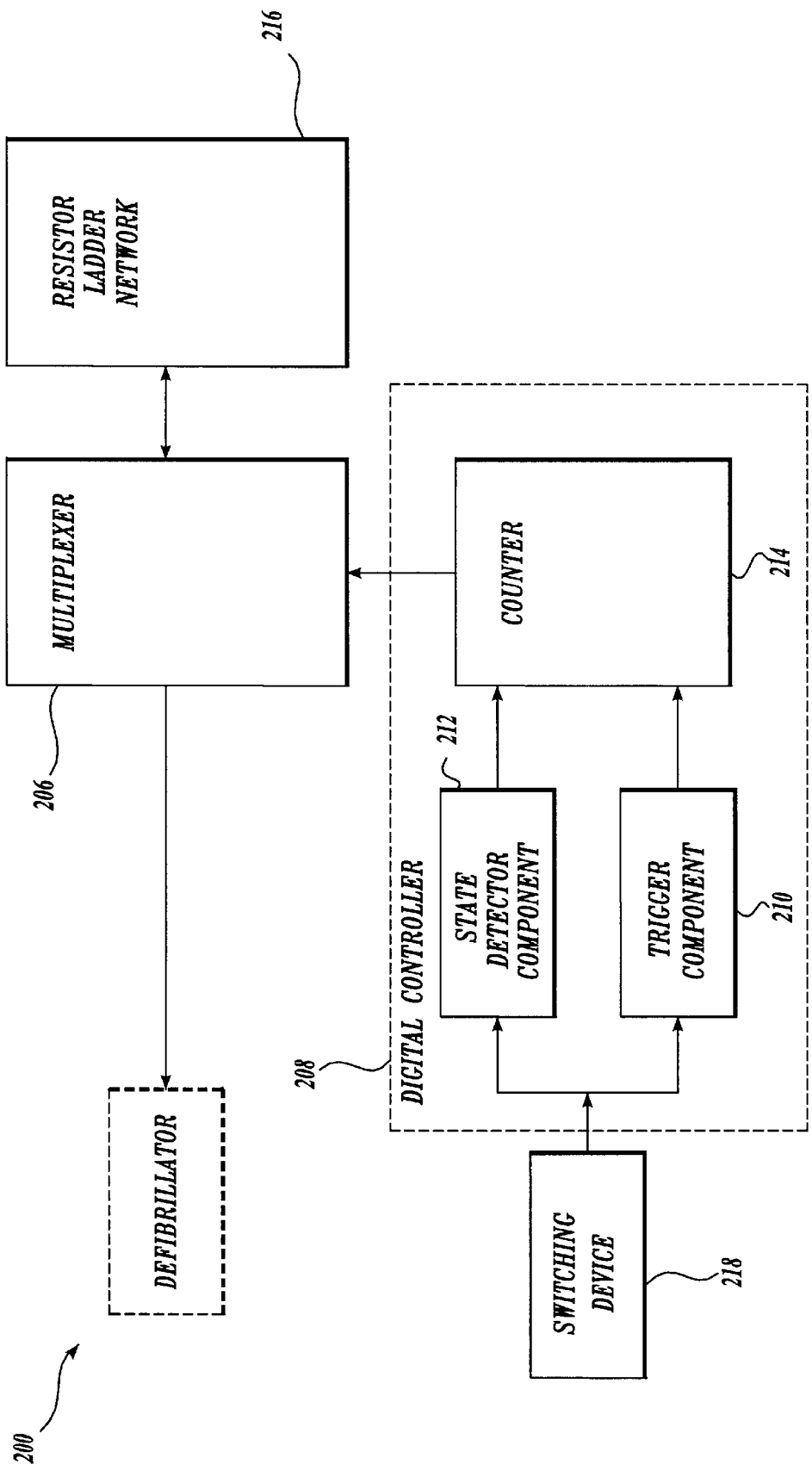
FIG. 5 is a block diagram illustrating an energy select control circuit in accordance with aspects of the present invention.

In the embodiment described above, the paddle 20 includes two energy level selector switches, an energy increase switch 164 and an energy decrease switch 166, activated by the actuators 152. The energy level selector switches 164 and 166 are mounted on the circuit 170 board and are electrically connected to an energy select circuit for determining the level of energy to be delivered to the patient. FIG. 5 is a block diagram illustrating components relating to one embodiment of an energy select circuit 200. The energy select circuit 200 includes a multiplexer 206 and a digital controller 208. The digital controller 208 receives an analog signal from a switching device 218, which includes the energy increase switch 164 and the energy decrease switch 166, and outputs a digital signal utilized by the multiplexer 206 to select one of a set of resistor networks. Depending on the digital input, the selected set of resistors in an associated resistor ladder network 216 provides an indicator voltage indicative of the desired energy level, which is outputted to the defibrillator. The defibrillator correlates the indicator voltage as either an increase or a decrease of one or more predefined energy level steps. Accordingly, the defibrillator increases or decreases the energy level of the electrotherapy signal delivered to the patient according to the predefined energy level steps.

In one embodiment of the present invention, the digital controller 208 of the energy select circuit 200 includes a trigger component 210, a state detector component 212, and a digital counter 214. The state detector component 212 receives an input from the switching device 218 and determines in which direction (increment or decrement) the value of the digital counter 214 will change. The trigger component 210, also receiving an input from the switching device 218, signals or "triggers" the digital counter 214 to change its present value, either incrementing or decrementing, based on the output of the state detector component 212. The digital counter 214, which keeps track of the previous energy level selected, adjusts the energy level according to the signal from the state detector component 212 and the trigger component 210 and outputs a new energy level to the multiplexer 206.

In an alternative embodiment, the output of the digital counter 214 may be utilized directly by the defibrillator circuitry of the defibrillator to generate the electrotherapy signal.

Figure 6:
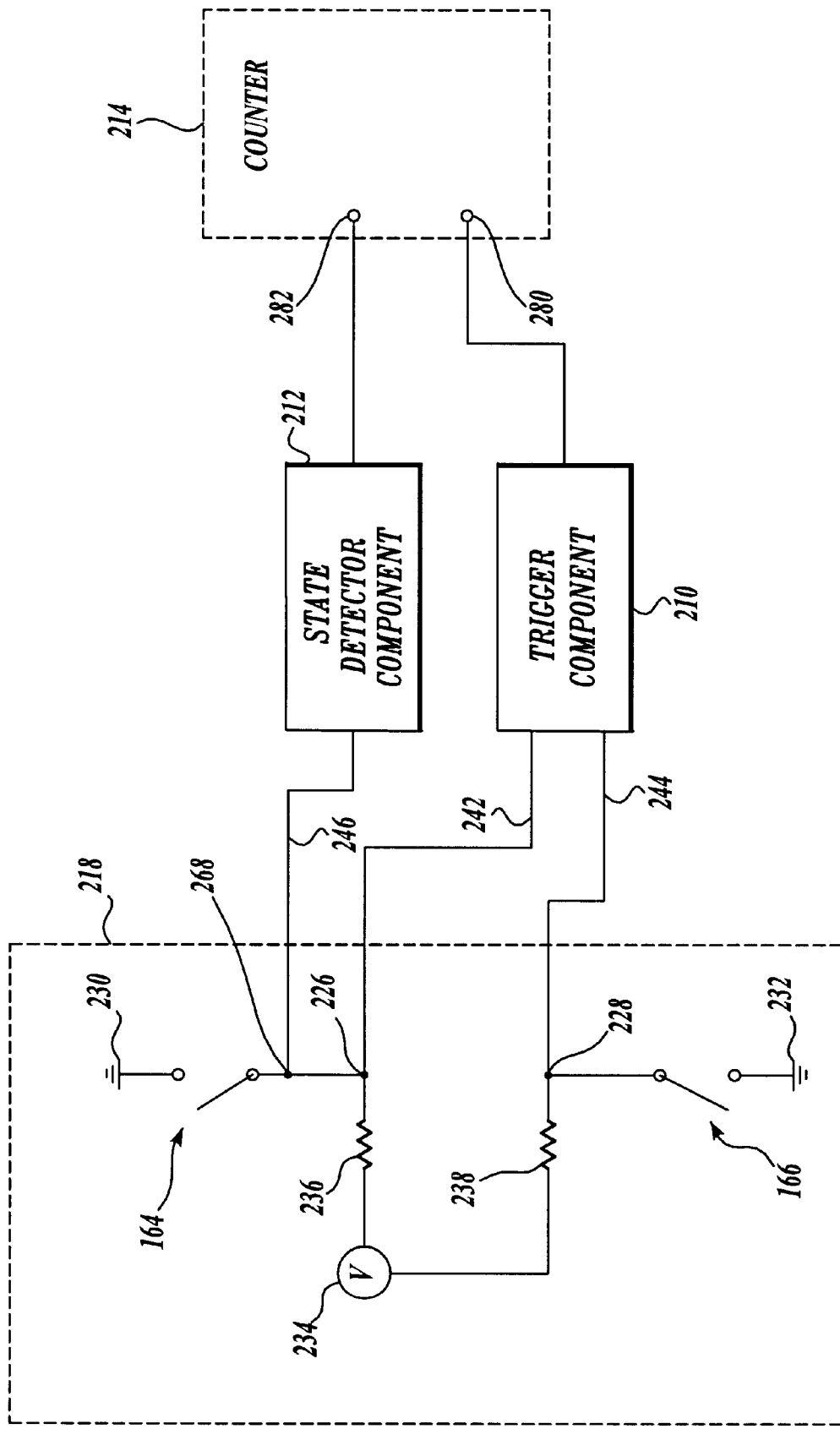
FIG. 6 is a circuit diagram of a switching device illustrated in the energy select control circuit of FIG. 5.

As shown in FIG. 6, the switching device 218 comprises the energy increase switch 164 and the energy decrease switch 166 connected in parallel with a source of voltage 234 through nodes 226 and 228, respectively. Each energy switch is grounded at 230 and 232, respectively. In the embodiment shown, the current from the voltage source 234 flows through resistors 236 and 238 before reaching the respective nodes 226 and 228. Connected to the respective nodes 226 and 228 are two signal outputs 242 and 244. The signal outputs 242 and 244 are connected to the trigger component 210, which will be described in more detail below. The switching device further includes a third signal output 246 connected in parallel with the energy increase switch 164 at node 268. The signal output 246 is connected to the state detector component 212, which will be described in more detail below.

The outputs 242, 244, and 246 of the switching device 218 are normally "high." Specifically, in steady state condition when neither switch is depressed, an open circuit occurs. Accordingly, since each output is connected in parallel with the voltage source 234, along with the switches 164 and 166, the current flows through each output, creating a "high" signal. In contrast, when one of the switches is depressed, e.g., the energy decrease switch 166, a circuit is closed due to the switch 166 being grounded at 232. Accordingly, the current flows through the switch 166 instead of flowing through signal output 244, thus creating a "low" signal at output 244.

Figure 7:
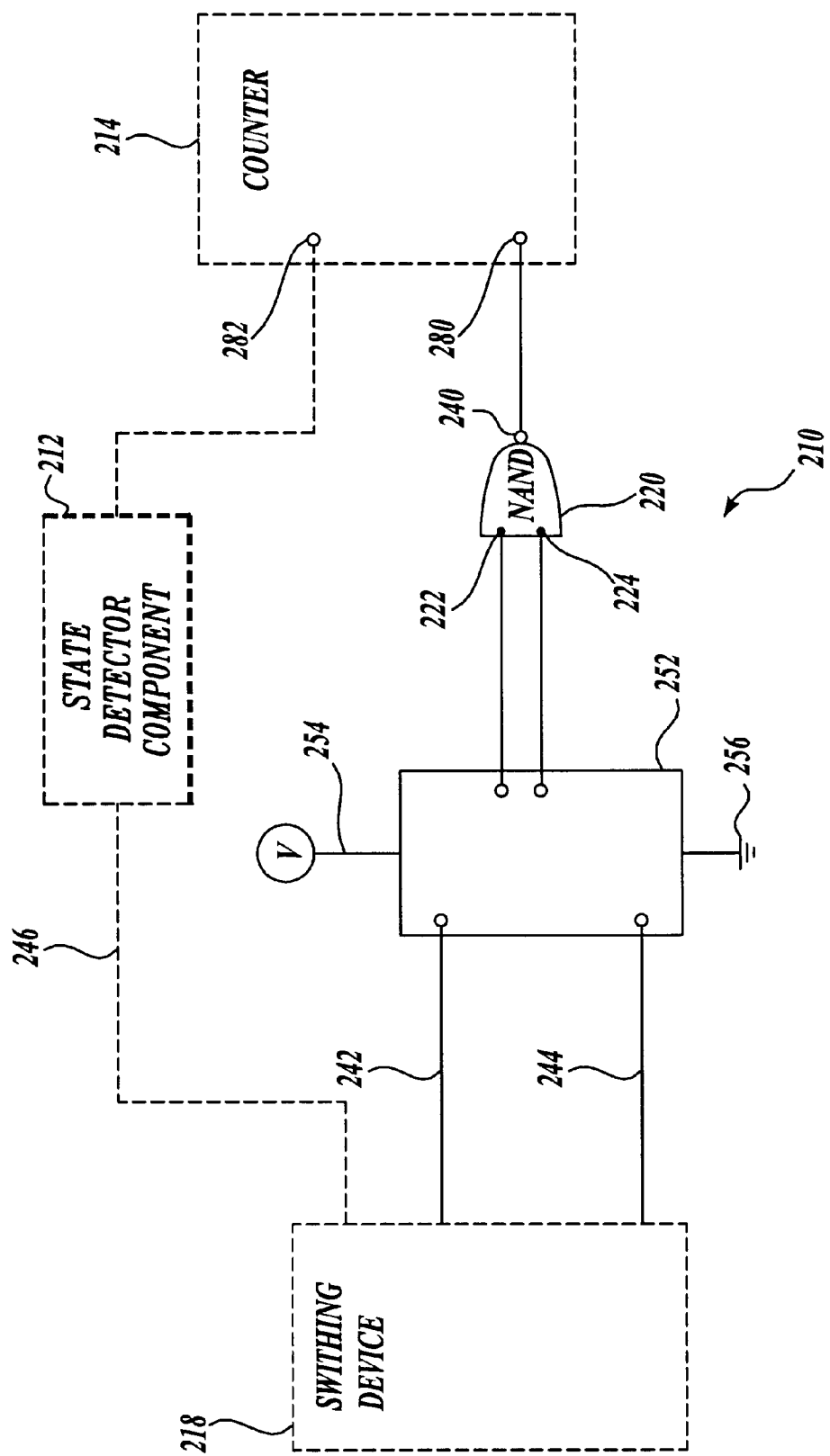
FIG. 7 is a circuit diagram of a trigger component illustrated in the energy select control circuit of FIG. 5.

Referring back to FIG. 5, the energy select circuit 200 further includes a trigger component 210 for signaling the digital counter to change its present value. In one embodiment of the present invention illustrated in FIG. 7, the trigger component comprises a NAND gate 220. As shown in FIG. 7, the NAND gate 220 includes two inputs 222 and 224. One input 222 is connected in parallel to the signal output 242 of the switching device 218, and the other input 224 is connected in parallel to the signal output 244 of the switching device 218. The signal outputs 242 and 244 supply a signal to the respective inputs 222 and 224 of the NAND gate 220.

As shown in FIG. 7, the NAND gate 220 further includes an output 240 which is connected to the input 280 of the digital counter 214. Other electrical circuit components may be included in the trigger component 210 such as a delay 252 for delaying the output signals 242 and 244 to the input 280 of the digital counter 214. The purpose of the delay 252 is to make sure that the parallel state detector component 212 has the chance to return to steady state before the trigger component "triggers" or signals the digital counter to change its present counter value. The delay 252 is powered by a voltage source through connection 254 and is grounded at 256. Although the delay 252 is shown as being disposed before the NAND gate 220, it will be appreciated that the delay 252 could be connected to the output 240 of the NAND gate 220, before reaching the input 280 of the digital counter 214.

In operation, as discussed above with reference to the switching device, when neither of the energy switches and the switching device 218 are depressed (steady state), an open circuit occurs at the switching device 218. Accordingly, both inputs 222 and 224 of the NAND gate 220 receive a "high" signal from the signal outputs 242 and 244 of the switching device 218, respectively. When the energy decrease switch is depressed (and the energy increase switch is not depressed), a current corresponding to the supply of voltage flows through the energy decrease switch due to the switch being grounded at 232. Accordingly, a low voltage is supplied to the second input 224 of the NAND gate 220. Therefore, the NAND gate 220 interprets the low voltage as a "0" at the second input 224 of the NAND gate 220. Since the energy increase switch is normally "high" (a voltage signal is received at the first input of the NAND gate), the output 240 of the NAND gate 220 outputs a "high" signal to the input 280 of the digital counter 214. The "high" signal instructs the digital counter 214 to decrement the present counter value based on the input received from the state detector component 212, which will be described in more detail below. Likewise, if the energy increase switch is depressed (and the energy decrease switch is not depressed), the NAND gate 220 outputs a "high" signal to the clock input 280 of the digital counter 214, thus incrementing the digital counter 214 as described above.

Figure 8:
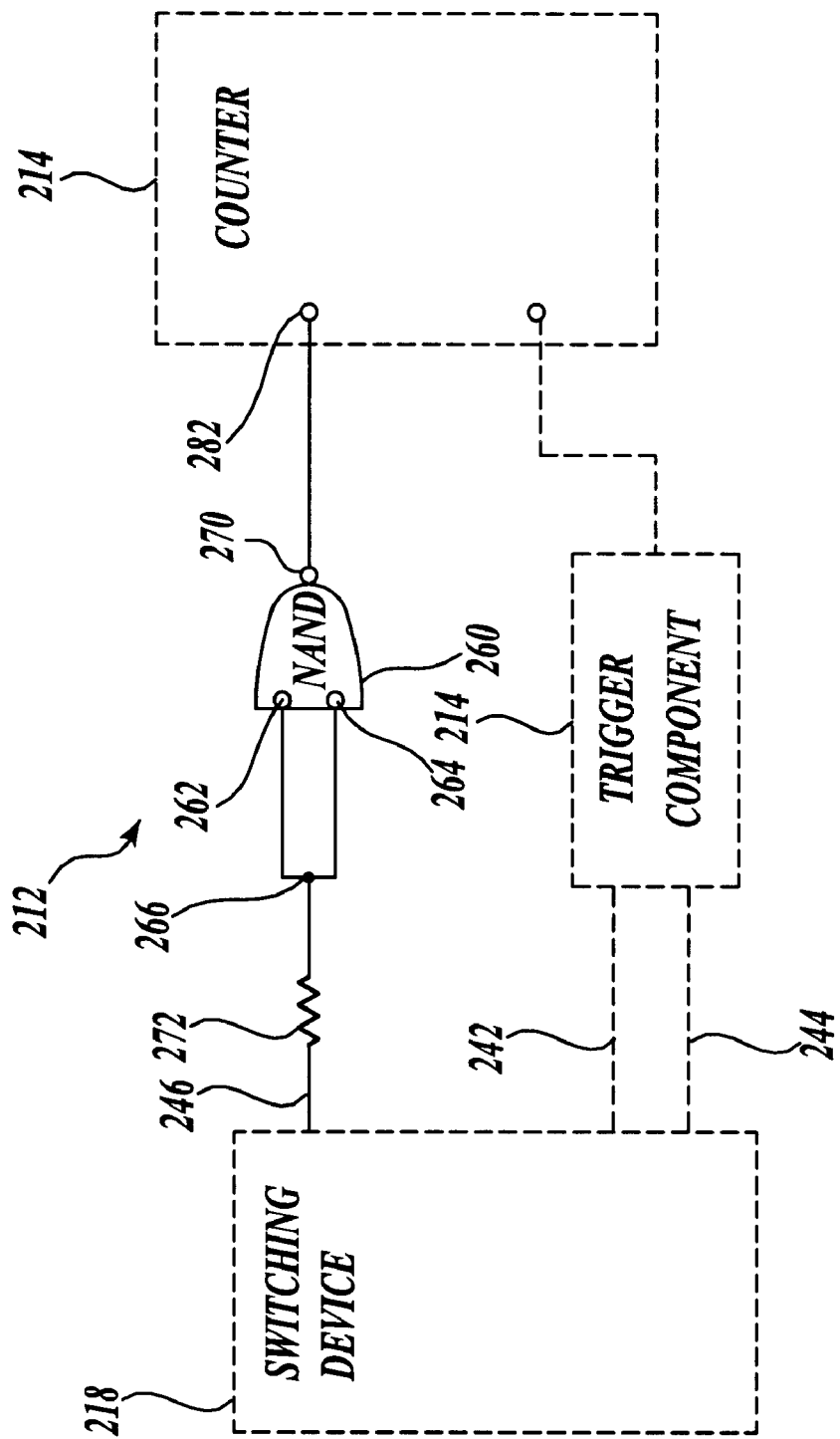
FIG. 8 is a circuit diagram of a state detector component illustrated in the energy select control circuit of FIG. 5.

Referring back to FIG. 5, the energy select circuit 200 further includes a state detector device 212 for capturing and transmitting which energy selector switch has been depressed. In one embodiment of the present invention illustrated in FIG. 8, the state detector component 212 comprises a NAND gate 260. As illustrated in FIG. 8, the NAND gate 260 includes two inputs 262 and 264 connected to a single node 266. The node 266 is connected in series to the signal output 246 of the switching device 218 so that each NAND gate input 262 and 264 has the same "high" or "low" signal. The output 270 of the NAND gate 260 is to the up/down input 282 of the digital counter 214. Other electrical circuit components may be included in the state detector component 212 such as a resistor 272 which is connected to the signal output 246 of the switching device 218 before node 266. Since the state detector component 212 is connected in parallel with the energy increase switch, the state of the energy increase switch (depressed, not depressed) controls what's inputted into the up/down input 282 of the digital counter 214.

In operation, when the energy increase switch is depressed (and the energy decrease switch is not depressed), a current corresponding to the supply of voltage flows through the energy increase switch due to the switch being grounded at 230. Accordingly, a low voltage is supplied to both inputs 262 and 264 of the NAND gate 260, whereby the NAND gate 260 interprets these inputs as "low." Accordingly, the NAND gate 260 outputs a "high" signal to the up/down input 282 of the digital counter 214. The counter 218 then interprets the "high" signal as "up", thus indicating that the energy increase switch was depressed. In contrast, when the energy decrease switch is either depressed or in its steady state (i.e., not depressed, and the energy increase switch is not depressed), the current corresponding to the voltage from the voltage source 234 is supplied to both inputs 262 and 264 of the NAND gate 260, whereby the NAND gate 260 interprets these inputs as "high." Accordingly, the NAND gate 260 outputs a "low" signal to the up/down input 282 of the digital counter 214. The counter then interprets the "low" signal as "down," thus indicating that the energy decrease switch was depressed or in its steady state. The counter also interprets this signal as the energy increase switch was not depressed.

Referring again to FIG. 5, the energy select circuit 200 further comprises a digital counter 214 for receiving inputs from the trigger component 210 and the state detector component 212, generating a signal corresponding to the inputs of the trigger and state detector devices, and outputting the generated signal to the multiplexer 206. In one embodiment of the present invention illustrated in FIG. 9, the digital counter 214 includes a plurality of inputs including the trigger input 280, and the up/down input 282. As described above, the up/down input 282 of the digital counter 214 receives a "high" or "low" signal from the state detector component 212. If the up/down input 282 of the digital counter 214 receives a "high" signal from the output 270 of the NAND gate 260, the digital counter 214 interprets this signal as "up" or that the energy increase switch was depressed. Likewise, if the up/down input 282 of the digital counter 214 receives a "low" signal from the output 270 of the NAND gate 260, the digital counter 214 interprets this signal as "down" or that the energy decrease switch was depressed.

Irrespective of the signal from the state detector component 212, the digital counter 214 will not register the change until the trigger component 210 generates a "high" signal and delivers the signal to the trigger input 280. For example, if the energy decrease switch is depressed, the input 280 of the digital counter 214 receives a "high" signal from the trigger component 210, the NAND gate 220, indicating that the counter should be decremented. Accordingly, since the energy decrease was depressed, the up/down input 282 of the counter receives a "low" signal from the state detector component 212, the NAND gate 260, thus instructing the counter to decrement the present value of the digital counter 214 by one unit.

Figure 9:
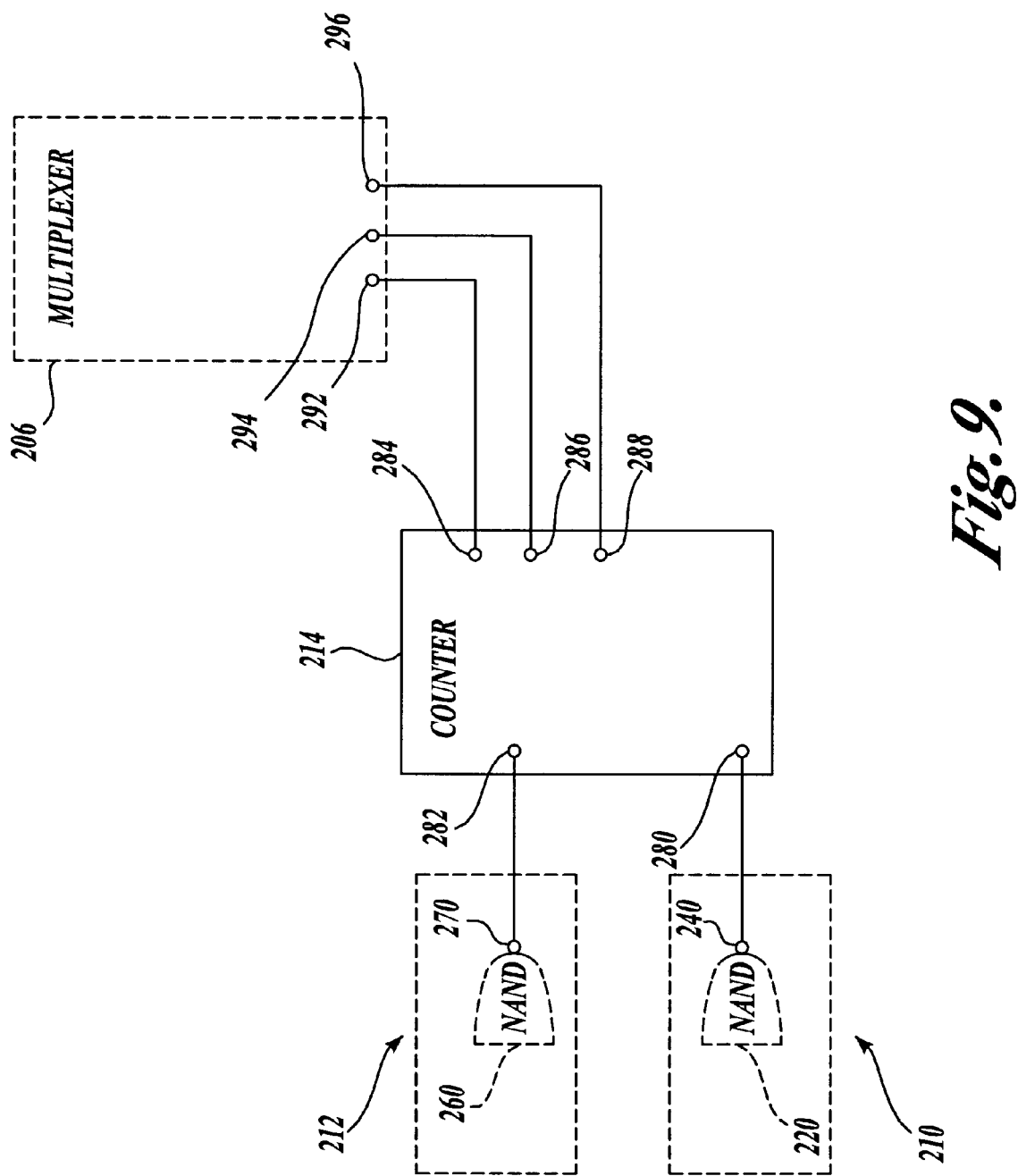
FIG. 9 is a circuit diagram of a counter illustrated in the energy select control circuit of FIG. 5.

As shown in FIG. 9, the digital counter 214 also includes a plurality of outputs for outputting the present counter setting to the multiplexer 206. In the embodiment shown, the digital counter 214 has three sequential outputs 284, 286, 288 that can output any one of eight different binary outputs which are inputted into the corresponding inputs 292, 294, 296, respectively, of the multiplexer 206. For example, if the present state of the counter is "002", the three outputs, 284, 286, 288, will output a "010". That is, 284 will output a value of "0", 286 will output a value of "1", and so on.

In an actual embodiment of the present invention, the digital counter 214 outputs only the first six outputs out of the eight possible outputs of the counter 214 so that the counter's number of possible outputs, i.e., "000", "001 ", "010", and so on, corresponds to the sets of resistors in the resistor ladder network, which will be described in more detail below. Additionally, the digital counter 214 includes an overflow/underflow feature, such that the digital counter 214 overflows after receiving a signal to increment while the digital counter 214 is at its highest counter state, or underflows after receiving a signal to decrement while the digital counter 214 is at its lowest counter state. For example, when the counter is at "101", its highest counter output value, and the operator depresses the energy increase switch, the digital counter 214 overflows to the lowest counter output value, i.e., "000". Likewise, when the counter is at "000", its lowest counter output value, and the operator depresses the energy decrease switch, the digital counter 214 underflows to the highest counter output value, i.e., "101". Further, it would be understood that the digital counter 214 may also include a reset feature, which can be used in any manner known in the art for resetting the digital counter.

Referring back to FIG. 5, the energy select circuit 200 further includes a multiplexer 206 for supplying a single variable voltage output to the defibrillator D. In one embodiment illustrated in FIG. 10, the multiplexer 206 includes a plurality of digital inputs for receiving the present counter setting output from the digital counter 214. As shown in FIG. 10, the multiplexer 206 has three sequential binary inputs 292, 294, 296 that can receive any one of a number different outputs from the corresponding outputs 284, 286, 288, respectively, of the digital counter 214. Additionally, the multiplexer 206 includes a plurality of analog inputs for receiving a variable voltage from a resistor ladder network 216. In the embodiment shown, the plurality of analog inputs includes inputs 300, 302, 304, 306, 308, and 310. The multiplexer 206 further includes an output 298 which outputs the single variable voltage received from the resistor ladder network 216 to the defibrillator D.

As shown in FIG. 10, the resistor ladder network 216 is comprised of a plurality of resistors connected in series, separated by nodes for outputting a single varying voltage to be inputted into the multiplexer 206. In the embodiment shown, five resistors, 312, 314, 316, 318, and 320, are connected together via nodes 322, 324, 326, 328, 330, and 332. The nodes 322, 324, 326, 328, 330, and 332, are connected to analog inputs 300, 302, 304, 306, 308, and 310 of the multiplexer 206, respectively, while node 322 is further connected to a source of voltage V. In an actual embodiment of the present invention, approximately 4.3 volts is supplied to node 322, and to input 300 via node 322. Resistors 312, 314, 316, 318, and 320 are selected such that voltages of approximately 3.7, 3.1, 2.5, 1.9, and 1.3 volts are supplied to inputs 302, 304, 306, 308, and 310, respectively.

Depending on the digital input received by the multiplexer 206 from the digital counter 214, a switch connected to the corresponding analog input is closed to complete a circuit causing the voltage connected to node 322 to be supplied through the resistors associated with the particular digital input and into the corresponding analog input of the multiplexer 206. For example, each counter output corresponds to an analog input, i.e. "000" corresponds to input 310, "001" corresponds to input 308, "010" corresponds to input 306, and so on. If the present counter value of the counter is "002", the counter outputs a "010" to the input of the multiplexer 206 and a switch connected to input 306 is closed. Accordingly, current from the voltage supplied at node 322 runs through resistors 312, 314, and 316, and into input 306 of the multiplexer 206. In an actual embodiment, approximately 2.5 volts are supplied to input 306.

The multiplexer 206 outputs the variable voltage received from resistor ladder network 216 via output 298 to the defibrillator D. Once the variable voltage, now referred to as the indicator voltage, is obtained by the defibrillator, the indicator voltage is interpreted by the defibrillator as either an increase or decrease in energy level from a previous selected energy level. Accordingly, the defibrillator increases or decreases the current energy level of the defibrillator D corresponding to a detected change in the indicator voltage. The defibrillator D delivers the adjusted energy level, in the form of an electrotherapy signal, to the patient when the trigger switch on each paddle is depressed. The electrotherapy signal is delivered to the electrode from the defibrillator via the electrical cord.

In an actual embodiment of the present invention, the "new"indicator voltage is compared to the previous indicator voltage and the difference is computed. This comparison may be accomplished by a defibrillator software memory component, analog circuitry, or a combination thereof. In either case, the defibrillator interprets the difference or change in indicator voltage as either an increase or a decrease in the energy level to be delivered to the patient. Accordingly, the defibrillator varies the energy level of the electrotherapy signal by predefined energy level steps according to the change in indicator voltage. For example, if the previous indicator voltage was 1.9 volts, and the new indicator voltage, generated via depressing the energy increase switch, is 2.5 volts, the defibrillator computes the difference or change, i.e., +0.6 volts, and determines the difference as an increase in the desired energy level to be delivered to the patient. Likewise, if the previous indicator voltage was 1.9 volts, and the new indicator voltage, generated via depressing the energy decrease switch, is 1.3 volts, the defibrillator computes the difference, i.e., −0.6 volts, and determines the difference as a decrease in the desired energy level to be delivered to the patient. Accordingly, depending on whether the energy increase switch or the energy decrease switch was depressed, the defibrillator either increases or decreases the current selected energy level of the defibrillator one predefined energy level step to reflect the desired selected energy level requested by the defibrillator operator.

In an actual embodiment of the present invention, some defibrillators may have a limited range of indicator input voltages that it can process. For example, a defibrillator may be able to accept an indicator voltage between approximately 1.3 volts and 4.3 volts. Additionally, to mitigate any potential errors in the selection of the energy levels, indicator voltage levels may be selected to have a greater value (e.g. 0.6 volts) than most environmental influences and variations in electrical components. Accordingly, in conjunction with one another, the defibrillator may be limited in the number of successive discrete indicator voltages that can be processed. With reference to the previous example, the defibrillator would only be capable of handling six discrete 0.6 volts indicator voltages between a voltage range of approximately 1.3 volts and 4.3 volts.

Although a defibrillator may be limited in the indicator voltage range, the defibrillator often has the capability to generate a greater number of predefined energy levels. Accordingly, in accordance with the present invention, the digital counter can also provide an overflow/underflow feature so that the defibrillator is able to select all of the predefined energy levels by being able to increment or decrement no matter what the current value of the indicator voltage is. The overflow/underflow feature either "rolls over" or "rolls back" the counter so that the indicator voltage remains within the necessary range. Additionally, the defibrillator is configured to interpret a difference greater than a single interval (e.g. 0.6 volts) as a rollover/rollback and will continue adjusting its discrete energy levels accordingly. For example, the defibrillator interprets an indicator voltage difference between its highest voltage state of 4.3 volts and a "new" state of 1.3 volts as an increase in the desired energy level of one step. Likewise, the defibrillator can interpret the difference in indicator voltages between its lowest voltage state of 1.3 volts and a "new" state of 4.3 volts as a decrease in the desired energy level.

While one suitable embodiment of the digital controller 208 has been described above with reference to FIGS. 5–10, it should be readily evident that other digital controllers could be used to receive a signal from the switching device, process the signal received from the switching device, and output a signal to the multiplexer causing a change in the energy level of the electrotherapy signal to be supplied by the defibrillator based on the processed signal.

While an illustrative embodiment of the invention has been illustrated and described, it will be appreciated that various changes can be made therein without departing from the spirit and scope of the invention.

The embodiments of the invention in which an exclusive property or privilege is claimed are defined as follows:

1. An electrotherapy delivery device comprising:
   a base member of substantially rectangular shape having a bottom surface, and diagonally opposed corners;
   an electrode coupled to said bottom surface of said base member; said electrode operable for delivering an electrical charge supplied thereto to a patient;
   an upper member defining a handle portion which comprises a grasping portion;
   a coupling mechanism that selectively couples said upper member to said base member such that said grasping portion of said handle portion extends diagonally across said base member and is aligned with two of said diagonally opposed corners of said base member; and
   at least one switch mechanism disposed within said upper member.

2. The device of claim 1, further comprising a second electrode, said second electrode being exposed when said base member is separated from said upper member.

3. The device of claim 2, wherein said upper member further comprises a mounting portion coupled to said handle portion, said second electrode coupled to said mounting portion.

4. The device of claim 3, wherein said base member includes a recess portion for receiving said mounting portion of said upper member.

5. The device of claim 3, wherein said upper member further comprises a boss having a bottom surface, said boss extending from said mounting portion, said second electrode coupled to said bottom surface of said boss.

6. The device of claim 5, wherein said base member includes a cavity, said second electrode nestable within said cavity when said base member is coupled to said upper member.

7. The device of claim 6, wherein said base portion comprises diametrically opposed inner side walls, and said coupling mechanism that selectively couples said base member to said upper member comprises two latch members, and slots positioned in said inner side walls, said latch members being translatable within said slots and biased to engage said boss.

8. The device of claim 7, wherein said boss includes diametrically opposed sides, and two spaced apart rib portions located on said diametrically opposed sides of said boss, said rib portions engagable with said latch members to couple said base member.

9. The device of claim 8, wherein inner surfaces of said diametrically opposed inner side walls of said base member includes two spaced-apart elongate rail members, said rail members being substantially parallel to said bottom surface of said base member, said rib portions of said boss being slidably engagable between said rail members when said base member is coupled to said upper member.

10. The device of claim 1, wherein said at least one switch mechanism is operable for supplying an electrical charge to said electrode.

11. The device of claim 10, further comprising an energy selector switch for increasing the electrical charge to said electrode and an energy selector switch for decreasing the electrical charge to said electrode, said energy selector switches operable to generate a selected energy level output.

12. The device of claim 11, further comprising an energy selection processing circuit for receiving said selected energy level output from said energy selector switches.

13. The device of claim 12, wherein said energy selection processing circuit includes a digital controller for receiving said selected energy level output from said energy selector switches and transmitting a digital signal corresponding to said selected energy level output; and a multiplexer for receiving said digital signal corresponding to said selected energy level output, determining said selected energy level based on said digital signal, and outputting a variable signal corresponding to said selected energy level to the defibrillator.

14. The device of claim 13, wherein said digital controller includes:
- a counter having a present counter value, said counter operable to output said present counter value;
- a trigger component operable for receiving said selected energy level output from said energy selector switches and transmitting a signal corresponding to said output to said counter for changing said present counter value;
- a state detector component operable for receiving said selected energy level output and transmitting a signal corresponding to said output to said counter for instructing said counter to increment or decrement said present counter value.

15. The device of claim 13, further comprising a resistor ladder network for transmitting said variable signal corresponding to said selected energy level to said multiplexer, said multiplexer outputting said variable signal to the defibrillator.

16. The device of claim 1, wherein said handle portion of said upper member further comprises a base portion and a cover portion, said base portion of said upper member defining a cavity for receiving said at least one switch mechanism.

17. In a defibrillator system having a pair of defibrillator paddles, an activation switch, and a defibrillator that can deliver a selectable level of energy to resuscitate a patient via a said pair of defibrillator paddles when an said activation switch is depressed, said selectable level of energy being controllable by one of said defibrillator paddles, said one paddle including a pair of energy selector switches operable to generate a selected energy level output, an energy selection processing circuit comprising:
- a digital controller for receiving said selected energy level output from said energy selector switches and transmitting a digital signal corresponding to said selected energy level output; and
- a multiplexer for receiving said digital signal corresponding to said selected energy level output, determining said selected energy level based on said digital signal, and outputting a variable signal corresponding to said selected energy level to the defibrillator,
- wherein said digital controller includes:
  - a counter having a present counter value, said counter operable to output said present counter value;
  - a trigger component operable for receiving said selected energy level output from said energy selector switches and transmitting a signal corresponding to said output to said counter for changing said present counter value;
  - a state detector component operable for receiving said selected energy level output and transmitting a signal corresponding to said output to said counter for instructing said counter to increment or decrement said present counter value.

18. The energy selection processing circuit of claim 17, further comprising a resistor ladder network for transmitting a variable signal corresponding to said selected energy level to said multiplexer, said multiplexer outputting said variable signal to the defibrillator.

19. An electrotherapy delivery device comprising:
- an adult electrode assembly having a bottom surface;
- a first electrode mounted to said bottom surface of said adult electrode assembly;
- a pediatric electrode assembly defining a handle portion which comprises a grasping portion, and a mounting portion;
- a coupling mechanism that selectively couples said pediatric electrode assembly to said adult electrode assembly;
- a second electrode mounted to said mounting portion; and
- at least one switch mechanism disposed within said device and in electrical communication with said second electrode,
- wherein said adult electrode assembly comprises diametrically opposed corners, and said pediatric electrode assembly is selectively coupled to said adult electrode assembly such that said grasping portion of said handle portion diagonally extends across said adult electrode assembly and is aligned with said diametrically opposed corners.

20. The device of claim 19, wherein said adult electrode assembly is of a substantial rectangular shape.

21. The device of claim 19, wherein said second electrode is exposed when said adult electrode assembly is separated from said pediatric electrode assembly.

22. The device of claim 19, wherein said adult electrode assembly includes a recess portion for receiving said mounting portion of said pediatric electrode assembly.

23. The device of claim 19, wherein said pediatric electrode assembly further comprises a boss having a bottom surface, said boss extending from said mounting portion, said second electrode coupled to said bottom surface of said boss.

24. The device of claim 23, wherein said adult electrode assembly includes a cavity, said second electrode nestable within said cavity when said adult electrode assembly is coupled to said pediatric electrode assembly.

25. The device of claim 19, wherein said handle portion of said pediatric electrode assembly further comprises a base portion and a cover portion, said base portion of said pediatric electrode assembly defining a cavity for receiving said at least one switch mechanism.

26. The device of claim 25, wherein said at least one switch mechanism comprises an activation switch mechanism for delivering an electrical shock to a patient, and an energy selector switch for increasing the electrical charge to said electrode and an energy selector switch for decreasing the electrical charge to said electrode, said energy selector switches operable to generate a selected energy level output.

27. The device of claim 26, further comprising an energy selection processing circuit for receiving said selected energy level output from said energy selector switches.

28. The device of claim 27, wherein said energy selection processing circuit includes a digital controller for receiving said selected energy level output from said energy selector switches and transmitting a digital signal corresponding to said selected energy level output; and
- a multiplexer for receiving said digital signal corresponding to said selected energy level output, determining said selected energy level based on said digital signal, and outputting a signal corresponding to said selected energy level to the defibrillator.

29. The device of claim 28, wherein said digital controller includes:
   a counter having a present counter value, said counter operable to output said present counter value;
   a trigger component operable for receiving said selected energy level output from said energy selector switches and transmitting a signal corresponding to said output to said counter for changing said present counter value;
   a state detector component operable for receiving said selected energy level output and transmitting a signal corresponding to said output to said counter for instructing said counter to increment or decrement said present counter value.

30. The device of claim 28, further comprising a resistor ladder network for transmitting a variable signal associated with said digital signal to said multiplexer, said multiplexer outputting said variable signal to the defibrillator.

31. An electrotherapy delivery device comprising:
   an adult electrode assembly having a bottom surface;
   a first electrode mounted to said bottom surface of said adult electrode assembly;
   a pediatric electrode assembly defining a handle portion and a mounting portion;
   a coupling mechanism that selectively couples said pediatric electrode assembly to said adult electrode assembly;
   a second electrode mounted to said mounting portion;
   a boss having a bottom surface, said boss extending from said mounting portion, said second electrode coupled to said bottom surface of said boss; and
   at least one switch mechanism disposed within said device and in electrical communication with said second electrode,
   wherein said adult electrode assembly comprises diametrically opposed inner side walls, and said coupling mechanism that selectively couples said adult electrode assembly to said pediatric electrode assembly comprises two latch members, and slots positioned in said inner side walls, said latch members being translatable within said slots and biased to engage said boss.

32. The device of claim 31, wherein said boss includes diametrically opposed sides, and two spaced apart rib portions located on said diametrically opposed sides of said boss, said rib portions engagable with said latch members to couple said adult electrode assembly to said pediatric electrode assembly.

33. The device of claim 32, wherein inner surfaces of said diametrically opposed inner side walls of said adult electrode assembly includes two spaced-apart elongate rail members, said rail members being substantially parallel to said bottom surface of said adult electrode assembly, said rib portions of said boss being slidably engagable between said rail members when said adult electrode assembly is coupled to said pediatric electrode assembly.

34. The device of claim 32, wherein said rib portions include an engagement surface, said engagement surface of said rib portions engaging with and displace said latch members from a first position to a second position.

35. A defibrillator system comprising:
   a defibrillator for generating a charge to be delivered to a patient;
   charge delivery devices of transmitting the charge generated by said defibrillator, said charge delivery devices stowable on a top surface of said defibrillator; said charge delivery devices including;
   a substantially rectangular base member having diagonally opposed corners;
   a handle which includes a grasping portion;
   a coupling mechanism that selectively couples said handle to said base member; and
   an electrode coupled to said base member;
   wherein said grasping portion of said handle extends diagonally across said base member and is aligned with two of said diagonally opposed corners of said base member.

36. The system of claim 35, further comprising a second electrode coupled to said handle, said second electrode being exposed when said base member is separated from said handle.

37. The system of claim 35, wherein said coupling mechanism includes spaced-apart rib portions coupled to said handle and two biased latch members disposed in slots within said base member.

38. The system of claim 37, wherein said coupling mechanism includes two sets of spaced-apart elongate rail members disposed within said base member, said rail members being substantially parallel to said electrode of said base member, said rib portions of said handle slidably engagable between said rail members when said base member is coupled to said handle.

* * * * *